United States Patent
Hidesaki et al.

(10) Patent No.: US 9,404,132 B2
(45) Date of Patent: Aug. 2, 2016

(54) METHOD FOR PRODUCING 1,5-PENTAMETHYLENEDIAMINE, 1,5-PENTAMETHYLENEDIAMINE, 1,5-PENTAMETHYLENE DIISOCYANATE, METHOD FOR PRODUCING 1,5-PENTAMETHYLENE DIISOCYANATE, POLYISOCYANATE COMPOSITION, AND POLYURETHANE RESIN

(75) Inventors: Tomonori Hidesaki, Singapore (SG); Akiko Natsuji, Mobara (JP); Toshihiko Nakagawa, Ichihara (JP); Goro Kuwamura, Chiba (JP); Daisuke Hasegawa, Ichihara (JP); Satoshi Yamasaki, Chiba (JP); Kuniaki Sato, Ichihara (JP); Hiroshi Takeuchi, Ichihara (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 13/581,554

(22) PCT Filed: Feb. 25, 2011

(86) PCT No.: PCT/JP2011/054388
§ 371 (c)(1),
(2), (4) Date: Aug. 28, 2012

(87) PCT Pub. No.: WO2011/108473
PCT Pub. Date: Sep. 9, 2011

(65) Prior Publication Data
US 2013/0079486 A1   Mar. 28, 2013

(30) Foreign Application Priority Data

Mar. 1, 2010   (JP) ................. 2010-044644

(51) Int. Cl.
C12P 13/00 (2006.01)
C07C 263/10 (2006.01)
(Continued)

(52) U.S. Cl.
CPC ............ *C12P 13/001* (2013.01); *C07C 263/10* (2013.01); *C08G 18/022* (2013.01); *C08G 18/089* (2013.01); *C08G 18/1875* (2013.01); *C08G 18/283* (2013.01); *C08G 18/3206* (2013.01); *C08G 18/701* (2013.01); *C08G 18/73* (2013.01); *C12N 1/005* (2013.01); *C12N 9/88* (2013.01); *Y02P 20/52* (2015.11)

(58) Field of Classification Search
None
See application file for complete search history.

(56) References Cited

U.S. PATENT DOCUMENTS

2005/0003497 A1   1/2005   Nishi et al.
2005/0287627 A1   12/2005   Hashimoto et al.
(Continued)

FOREIGN PATENT DOCUMENTS

JP   58-129972   8/1983
JP   01-132394   5/1989
(Continued)

OTHER PUBLICATIONS

Room Temperature (2008).*
(Continued)

*Primary Examiner* — Jeffrey Washville
(74) *Attorney, Agent, or Firm* — Foley & Lardner LLP

(57) ABSTRACT

In a method for producing 1,5-pentamethylenediamine, a lysine decarboxylase-expressing microorganism that is subjected to a treatment is used.

1 Claim, 2 Drawing Sheets

(51) Int. Cl.
   *C08G 18/02*   (2006.01)
   *C08G 18/70*   (2006.01)
   *C08G 18/73*   (2006.01)
   *C12N 9/88*    (2006.01)
   *C08G 18/08*   (2006.01)
   *C08G 18/18*   (2006.01)
   *C08G 18/28*   (2006.01)
   *C08G 18/32*   (2006.01)
   *C12N 1/00*    (2006.01)

(56) References Cited

U.S. PATENT DOCUMENTS

2009/0292100 A1* 11/2009 Fiene et al. ............ 528/85
2010/0292429 A1* 11/2010 Volkert et al. .......... 528/44

FOREIGN PATENT DOCUMENTS

| | | |
|---|---|---|
| JP | 2004-000114 | 1/2004 |
| JP | 2004-208646 | 7/2004 |
| JP | 2005-6650 | 1/2005 |
| JP | 2009/545553 | 12/2009 |
| WO | WO 2006/001382 A1 | 1/2006 |
| WO | WO/2009/092793 A2 | 7/2009 |

OTHER PUBLICATIONS

European Communication with Supplementary Extended European Search Report, European Patent Application No. 11 75 583.4, dated Jun. 19, 2013, (5 pages).
International Search Report PCT/JP2011/054388 dated Mar. 22, 2011.

* cited by examiner

METHOD FOR PRODUCING 1,5-PENTAMETHYLENEDIAMINE, 1,5-PENTAMETHYLENEDIAMINE, 1,5-PENTAMETHYLENE DIISOCYANATE, METHOD FOR PRODUCING 1,5-PENTAMETHYLENE DIISOCYANATE, POLYISOCYANATE COMPOSITION, AND POLYURETHANE RESIN

CROSS REFERENCE TO RELATED APPLICATIONS

The subject application is the U.S. National Phase of PCT/JP2011/054388 filed Feb. 25, 2012, which claims priority to Japanese Patent Application No. 2010-044644 filed Mar. 1, 2010. Each of which is incorporated herein by reference in entirety.

TECHNICAL FIELD

The present invention relates to a method for producing 1,5-pentamethylenediamine; 1,5-pentamethylenediamine; 1,5-pentamethylene diisocyanate; a method for producing 1,5-pentamethylene diisocyanate; a polyisocyanate composition; and a polyurethane resin.

BACKGROUND ART 1,5-Pentamethylene diisocyanate (PDI), and modified substance (e.g., a polyisocyanate composition such as isocyanurate) obtained by modifying 1,5-pentamethylene diisocyanate are used as a material of, for example, polyurethane resins.

1,5-Pentamethylene diisocyanate is produced, industrially, for example, by phosgenation of 1,5-pentamethylenediamine (PDA).

Furthermore, 1,5-pentamethylenediamine, i.e., a material of 1,5-pentamethylene diisocyanate, is gaining attention as a material of polymer derived from biomass, for example, as a material of polyurethane, a material of polyamide, etc.; and is produced, for example, by biochemical methods such as fermentation and enzymatic method.

As a method for producing 1,5-pentamethylenediamine, for example, a method in Patent Document 1 below is known: lysine decarboxylase acts on lysine as a substrate to be converted to 1,5-pentamethylenediamine (also called: 1,5-diaminopentane, cadaverine).

In the enzymatic decarboxylation of lysine, cells that express lysine decarboxylase may be used; however, it has been known that even if the cells that express lysine decarboxylase are not used in a larger amount, by giving treatments to these cells, compared with the case without treatment, reactivity per unit cell can be improved. The reactivity per unit cell indicates reaction yield and production rate per cell that expresses lysine decarboxylase. As such methods for treating cells, for example, the following methods have been proposed: a method in which cells are disrupted by ultrasonic treatment, using Dyno Mill, French Press, etc. (see Patent Document 1 below), or a method in which cells are treated with additives such as an organic solvent, a surfactant, etc. (see Patent Document 2 below).

Furthermore, for example, a method in which bacterial cells collected by centrifugal separation were frozen at −80° C., and thawed on ice when in use (see Patent Document 2 below) has been known.

As still another method that has been proposed is a method in which *Escherichia coli* in which lysine decarboxylase is localized on cell surface is used to improve reactivity (see Patent Document 1 below).

For example, Patent Document 1 below shows that when recombinant *Escherichia coli* in which lysine decarboxylase is expressed in the cells are collected from a culture solution and allowed to act on L-lysine hydrochloride without any treatment, the yield of 1,5-pentamethylenediamine was 15% with a reaction for 150 hours and the production rate was 0.001 mol/L·hr. On the other hand, it has been clarified that reactivity improves as follows: when using cell-disrupted solution subjected to ultrasonic treatment, the yield was 53% with a reaction for 10 hours, and the production rate was 0.072 mol/L·hr; and when *Escherichia coli* in which lysine decarboxylase was localized on cell surface was used, the yield was 90% with a reaction for 72 hours, and the production rate was 0.017 mol/L·hr.

CITATION LIST

Patent Document

Patent Document 1: Japanese Unexamined Patent Publication No. 2004-114
Patent Document 2: Japanese Unexamined Patent Publication No. 2005-6650

SUMMARY OF THE INVENTION

Problem to be Solved by the Invention

Although the above-described methods have been proposed as methods for improving reactivity in decarboxylation of lysine, these methods are not industrially advantageous.

For example, in the method in which cells are subjected to disruption treatment, in addition to its requirement of an industrial-scale special expensive cell disruption apparatus, operation of disruption treatment is troublesome and uneconomical.

In the method in which cells are treated with additives, in order to isolate and purify 1,5-pentamethylenediamine, steps of removing additives, which are troublesome operations, are necessary, and the steps are complicated.

In the method in which *Escherichia coli* in which lysine decarboxylase is localized on the cell surface is used, compared with the method in which *Escherichia coli* expressing enzyme in the cells is used, the level of expression of a lysine decarboxylase per cell to be used becomes low, and the cells have to be produced in a large amount to that extent and added to the reaction. When the amount of cells to be added to the reaction increases, the amount of impurities such as proteins derived from the cells inevitably increases, and loads increase in the step of removing cells or impurities derived from cells. In addition, when the removal of cells or impurities derived from cells is insufficient, quality of 1,5-pentamethylenediamine or polymers produced therefrom as a material may be reduced.

At the same time, importantly, it has been known that the treatment may deactivate the enzyme itself or decrease the activities of the enzyme. Thus the decrease in the enzyme activities limits improvement in reactivity per unit cell.

The present invention aims to provide a method for producing 1,5-pentamethylenediamine in which decrease in the activities of enzyme itself is suppressed to the minimum, using cells that express lysine decarboxylase treated with an industrially advantageous method, and achieving improvement in reactivity per unit cell, and 1,5-pentamethylenediamine is produced from lysine with high production rate and high reaction yield; 1,5-pentamethylenediamine obtained by the production method; 1,5-pentamethylene diisocyanate and a polyisocyanate composition produced from the obtained 1,5-pentamethylenediamine; a method for producing 1,5-pentamethylene diisocyanate; and a polyurethane resin obtained by using 1,5-pentamethylene diisocyanate and the polyisocyanate composition.

Means for Solving the Problem

As a result of an energetic study, the present inventors found that by highly densifying cells at the time of heat treatment, reduction in enzyme activities can be suppressed almost completely even if a heat treatment is conducted at a temperature that usually reduces enzyme activities. The present inventors found that by giving a heat treatment under such particular conditions, while keeping the enzyme activities, reactivity per cell can be drastically improved, thereby completing the present invention. Furthermore, the present inventors found that by highly densifying cells also in freeze-thaw treatment, while suppressing reduction in lysine decarboxylase activities, reactivity per cell can be drastically improved, thereby completing the present invention. Furthermore, the present inventors found that by treating cells with a high lysine salt concentration, completely unexpectedly, living cells are easily affected, and reactivity per cell can be drastically improved, thereby completing the present invention. Furthermore, the present inventors found that by conducting such a treatment, singly or in combination of two or more on cells that express lysine decarboxylase, and by using the cells treated as such, reactivity per cell in lysine decarboxylation is improved.

That is, the present invention is as follows:

[1] A method for producing 1,5-pentamethylenediamine, using a lysine decarboxylase-expressing microorganism that is subjected to a treatment;

[2] The method for producing 1,5-pentamethylenediamine according to [1], wherein the treatment is at least one or more of a freeze-thaw treatment, a heat treatment, and a lysine salt treatment;

[3] The method for producing 1,5-pentamethylenediamine according to [2], wherein the freezing temperature in the freeze-thaw treatment is −80° C. or more and a solidification point or less of the lysine decarboxylase-expressing microorganism or its suspension;

[4] The method for producing 1,5-pentamethylenediamine according to [2], wherein the dry bacterial cell-based concentration in the freeze-thaw treatment is 3 mass % or more and 25 mass % or less;

[5] The method for producing 1,5-pentamethylenediamine according to [2], wherein in the freeze-thaw treatment, the freezing temperature is more than −80° C., and/or the dry bacterial cell-based concentration is below 25 mass %;

[6] The method for producing 1,5-pentamethylenediamine according to [2], wherein in the freeze-thaw treatment, the freezing temperature and the dry bacterial cell-based concentration satisfy the following condition of (a) or (b), (a) a freezing temperature of −80° C. or less and a dry bacterial cell-based concentration of 3 mass % or more and 15 mass % or less, or (b) a freezing temperature of −10° C. or less and −30° C. or more and a dry bacterial cell-based concentration of 3 mass % or more and 25 mass % or less.

[7] The method for producing 1,5-pentamethylenediamine according to [2], wherein the heat treatment temperature is 50° C. or more and below 70° C.;

[8] The method for producing 1,5-pentamethylenediamine according to [2], wherein the dry bacterial cell-based concentration in the heat treatment is 12.5 mass % or more;

[9] The method for producing 1,5-pentamethylenediamine according to [2], wherein the lysine salt in the lysine salt treatment is lysine hydrochloride;

[10] The method for producing 1,5-pentamethylenediamine according to [2], wherein the lysine salt treatment is a lysine hydrochloride treatment in which a 32 mass % or more aqueous solution of lysine hydrochloride is brought into contact;

[11] The method for producing 1,5-pentamethylenediamine according to [1], wherein 1,5-pentamethylenediamine is extracted from an aqueous solution containing 1,5-pentamethylenediamine using a monohydric alcohol having 4 to 7 carbon atoms without conducting a heat treatment of 90° C. or more;

[12] 1,5-Pentamethylenediamine obtained by the above-described method for producing 1,5-pentamethylenediamine;

[13] 1,5-Pentamethylene diisocyanate obtained by phosgenating the above-described 1,5-pentamethylenediamine;

[14] 1,5-Pentamethylene diisocyanate obtained by carbamation and thermal decomposition of the above-described 1,5-pentamethylenediamine, the 1,5-pentamethylene diisocyanate including an antioxidant, and an acid compound and/or a compound having a sulfonamide group;

[15] The 1,5-pentamethylene diisocyanate according to [14], wherein the 1,5-pentamethylenediamine is extracted using an extractant, and the extractant in the extraction is a reaction material in the carbamation;

[16] A polyisocyanate composition obtained by modifying the 1,5-pentamethylene diisocyanate, the polyisocyanate composition including: at least one of the functional groups of (a) to (e) below, (a) an isocyanurate group,
(b) an allophanate group,
(c) a biuret group,
(d) a urethane group, and
(e) a urea group.

[17] A polyurethane resin obtained by allowing the above-described 1,5-pentamethylene diisocyanate to react with an active hydrogen compound;

[18] A polyurethane resin obtained by allowing the above-described polyisocyanate composition to react with an active hydrogen compound;

[19] A method for producing 1,5-pentamethylene diisocyanate, by phosgenating 1,5-pentamethylenediamine obtained by extraction from an aqueous solution containing 1,5-pentamethylenediamine using a monohydric alcohol having 4 to 7 carbon atoms without conducting a heat treatment of 90° C. or more;

[20] A method for producing 1,5-pentamethylene diisocyanate, by carbamation and thermal decomposition of 1,5-pentamethylenediamine obtained by extraction from an aqueous solution containing 1,5-pentamethylenediamine using a monohydric alcohol having 4 to 7 carbon atoms without conducting a heat treatment of 90° C. or more;

[22] The method for producing 1,5-pentamethylene diisocyanate according to [21], further blending an antioxidant, and an acid compound and/or a compound having a sulfonamide group;

[23] The method for producing 1,5-pentamethylene diisocyanate according to [21], wherein the 1,5-pentamethylenediamine is extracted by using an extractant, and the extractant in the extraction is used as a reaction material in the carbamation.

Effects of the Invention

With the present invention, 1,5-pentamethylenediamine can be produced from lysine at high production rates and high reaction yield by using lysine decarboxylase-expressing cells that were treated with an industrially advantageous method.

Furthermore, with the present invention, by using 1,5-pentamethylenediamine obtained at high production rates and high reaction yield, 1,5-pentamethylene diisocyanate can be obtained at high production rates and at high reaction yield.

Furthermore, 1,5-pentamethylene diisocyanate, a polyisocyanate composition, and a polyurethane resin of the present invention are produced by using 1,5-pentamethylenediamine obtained at high production rates and high reaction yield as a material, and therefore they can be obtained at high production rates and high reaction yield.

EMBODIMENT OF THE INVENTION

Figure 1:
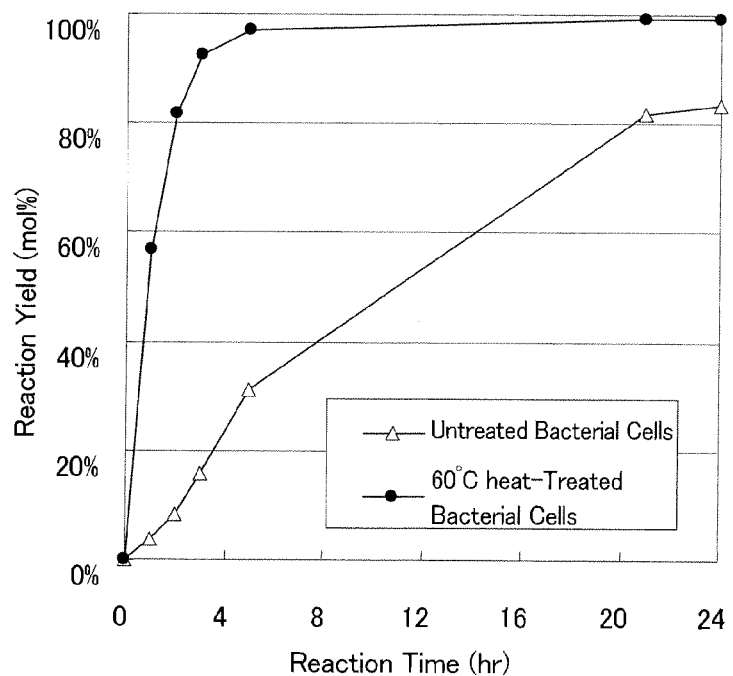
FIG. 1 is a diagram illustrating the relationships between time and yield in the reaction using untreated bacterial cells and 60° C. heat-treated bacterial cells.

The present invention is described in detail in the following.

In the method of the present invention, cells that express lysine decarboxylase (lysine decarboxylase-expressing microorganism) are treated, for example, by at least one or more of the heat treatment, freeze-thaw treatment, and lysine salt treatment, and by using the cells treated as such, 1,5-pentamethylenediamine (hereinafter, may be simply referred to as pentamethylenediamine) is produced using lysine as a substrate.

With the present invention, by using the cells subjected to the above-described treatment, 1,5-pentamethylenediamine can be produced at high reaction yield and at high production rates compared with those without treatment.

The heat treatment, freeze-thaw treatment, or lysine salt treatment in the present invention is not particularly limited, as long as the method allows for improvement in lysine decarboxylase activity in treated cells per dry bacterial cell-based weight, and stable lysine decarboxylase.

Examples of such methods are shown below.

The heat treatment in the present invention is cell incubation at 46° C. or more and below 75° C., preferably at 50° C. or more and below 70° C.

The heat treatment may be conducted on the cells before addition to a substrate solution, or may be conducted on a reaction liquid in which cells are added and reaction has started. For example, the reaction liquid may be incubated temporary at the above-described temperature.

Heat treatment time is usually for 10 minutes or more, preferably for 10 minutes or more and 60 minutes or less.

The form of the cells that are subjected to heat treatment is not particularly limited, and examples thereof include the cells as is obtained by centrifugal separation from a culture solution, and a cell suspension in which cells obtained from a culture solution by centrifugal separation are suspended in a solvent (e.g., water, buffer solution, etc.).

The dry bacterial cell-based concentration of the cell suspension is not particularly limited. For example, the dry bacterial cell-based concentration of the cell suspension is 0.025 mass % or more, preferably 0.25 mass % or more, more preferably 1.0 mass % or more, particularly preferably 12.5 mass % or more.

In the freeze-thaw treatment of the present invention, the freezing temperature is a solidification point or less of the cell or a suspension thereof, to be specific, −180° C. or more and the solidification point or less, preferably −90° C. or more and the solidification point or less, more preferably −80° C. or more and the solidification point or less, more preferably −70° C. or more and the solidification point or less, even more preferably −40° C. or more and the solidification point or less, and particularly preferably −30° C. or more and −10° C. or less. The thawing temperature is a solidification point or more of the cell or a suspension thereof, preferably the solidification point or more and below 80° C., more preferably the solidification point or more and 75° C. or less, even more preferably the solidification point or more and 70° C. or less.

The dry bacterial cell-based concentration of the cell suspension to be subjected to freeze-thaw treatment is not particularly limited. The dry bacterial cell-based concentration of the cell suspension to be subjected to freeze-thaw treatment is, for example, 1.2 mass % or more, preferably 3 mass % or more and 25 mass % or less, more preferably 3 mass % or more and below 25 mass %, even more preferably 3 mass % or more and below 20 mass %, particularly preferably 3 mass % or more and 15 mass % or less.

The freeze-thaw conditions are as follows: preferably a freezing temperature of more than −80° C., and/or a dry bacterial cell-based concentration of below 25 mass %. The conditions are satisfied when a freezing temperature is more than −80° C., or when a dry bacterial cell-based concentration is below 25 mass %, and the conditions also include a freezing temperature of more than −80° C. and a dry bacterial cell-based concentration of below 25 mass %.

More preferably, the freeze-thaw conditions satisfy the following conditions of the freezing temperature and the dry bacterial cell-based concentration of (a) or (b).

(a) a freezing temperature of −80° C. or less and a dry bacterial cell-based concentration of 3 mass % or more and 15 mass % or less.

(b) a freezing temperature of −10° C. or less and −30° C. or more and a dry bacterial cell-based concentration of 3 mass % or more and 25 mass % or less.

Such a freeze-thaw treatment achieves ensuring excellent cell activity.

In the freeze-thaw treatment, partially frozen cells are sufficient.

Furthermore, along with the freeze-thaw treatment, the cells can be cryopreserved. For example, the cells obtained by centrifugal separation from a culture solution can be frozen, cryopreserved for a predetermined period until used for reaction, and thawed right before the use for reaction.

For thawing, the frozen cells as is can be added to a substrate solution containing lysine and pyridoxal phosphate. In this manner, progress of lysine decarboxylation can be achieved while thawing the cells, which allows for easy and efficient operation.

The lysine salt treatment in present invention is suspending cells in a solvent (e.g., water, buffer solution, etc.) containing lysine salt.

The lysine salt concentration is, for example, 10 mass % or more and below 75 mass %, preferably 25 mass % or more and 75 mass % or less, more preferably 30 mass % or more and 70 mass % or less, even more preferably 32 mass % or more and 65 mass % or less.

Examples of lysine salts used in the lysine salt treatment include, for example, hydrochloride, acetate, carbonate, hydrogencarbonate, sulfate, nitrate, etc. of lysine, and preferably, hydrochloride of lysine is used.

The lysine salt treatment can also be performed in a reaction liquid in which enzymatic decarboxylation of lysine takes place. For example, by adding cells or treated cells to a substrate solution containing a lysine salt at the above-described concentration and pyridoxal phosphate, cells can be subjected to the lysine salt treatment, while allowing progress of lysine decarboxylation at the same time.

The treatment of the present invention can be performed by the above methods, and these treatments can be performed singly or in combination of two or more. In an example of the combinations, the cells subjected to the freeze-thaw treatment are added to a solution containing a lysine salt at the above-described concentration and pyridoxal phosphate, allowing the reaction to start. Reactivity per cell in lysine decarboxylation can be improved in this manner.

1,5-pentamethylenediamine produced in the present invention may be a salt thereof. Examples of salts of 1,5-pentamethylenediamine include hydrochloride, acetate, carbonate, hydrogencarbonate, sulfate, and nitrate of 1,5-pentamethylenediamine.

As a salt of 1,5-pentamethylenediamine, preferably, hydrochloride of 1,5-pentamethylenediamine is used.

The lysine used as a material in the present invention may be a salt thereof. Examples of lysine salts include hydrochloride, acetate, carbonate, hydrogencarbonate, sulfate and nitrate of lysine.

As the lysine salt, preferably, hydrochloride of lysine is used.

The lysine concentration in the reaction liquid is not particularly limited, for example, 1 mass % to 70 mass %, preferably 2 mass % to 50 mass %.

Lysine decarboxylase is an enzyme that converts lysine to 1,5-pentamethylenediamine, and is not particularly limited. Examples of lysine decarboxylases include those derived from a known organism. Specific examples of lysine decarboxylases include those derived from microorganism, such as *Bacillus halodurans*, *Bacillus subtilis*, *Escherichia coli*, *Selenomonas ruminantium*, *Vibrio cholerae*, *Vibrio parahaemolyticus*, *Streptomyces coelicolor*, *Streptomyces pilosus*, *Eikenella corrodens*, *Eubacterium acidaminophilum*, *Salmonella typhimurium*, *Hafnia alvei*, *Neisseria meningitidis*, *Thermoplasma acidophilum*, *Pyrococcus abyssi*, and *Corynebacterium glutamicum*. In view of safety, preferably, those derived from *Escherichia coli* is used.

Cells that express lysine decarboxylase can be produced by a known method, for example, in conformity with the description of Japanese Unexamined Patent Publication No. 2004-114.

Examples of methods for producing cells that express lysine decarboxylase include, to be more specific, a method in which recombinant cells that highly express lysine decarboxylase are cultured in a known medium, and thereafter, the proliferated recombinant cells are collected by centrifugal separation.

In such a method, the recombinant cells are not particularly limited, and examples thereof include those derived from microorganisms, animals, plants, or insects. To be more specific, for example, when animals are used, such examples include mise, rats, and cultured cells thereof; when plants are used, such examples include *Arabidopsis thaliana*, *Nicotiana tabacum*, and cultured cells thereof; when insects are used, such examples include *Bombyx* and cultured cells thereof; and when microorganisms are used, such examples include *Escherichia coli*.

These recombinant cells may be used singly or in combination of two or more.

As a method of increasing lysine decarboxylase activity in the cells, for example, the enzyme amount of lysine decarboxylase is increased.

The enzyme amount in the cells is increased, for example, by improving the transcriptional regulatory region in genes, increasing the copy number of genes, or efficient translation to protein.

In the improvement in transcriptional regulatory region, modification is added to increase the gene transcription amount, for example, by introducing a mutation in a promoter, the promoter is reinforced, thereby increasing the gene transcription amount in downstream. Other than introducing a mutation in the promoter, a highly expressing promoter in the host can be introduced. Examples of promoters include, to be more specific, in *Escherichia coli*, lac, tac, and trp. Also, an enhancer can be newly introduced to increase the transcription amount of the genes. Introduction of genes such as chromosomal DNA promoter can be performed in conformity with, for example, Japanese Unexamined Patent Publication No. H1-215280.

Increase in the copy number of genes can be achieved, to be specific, by forming recombinant DNAs by connecting genes to a multi-copy vector, and allowing the host cell to hold the recombinant DNA. Vectors includes those widely used, including plasmid, phage, etc., and also include, other than those, for example, transposon (Berg, D. E and Berg. C. M., Bio/Technol., vol. 1, P. 417 (1983)) and Muphage (Japanese Unexamined Patent Publication No. H2-109985). Furthermore, the copy number can be increased by introducing genes into chromosomes with a method using a plasmid for homologous recombination.

As a method for increasing protein translation efficiency, examples include, introducing and modifying, in procaryotes, SD sequence (Shine, J. and Dalgarno, L., Proc. Natl. Acad. Sci. USA, 71, 1342-1346 (1974)), in eucaryotes, Kozak consensus sequence (Kozak, M., Nuc. Acids Res., Vol. 15, p. 8125-8148 (1987)), and also optimizing codon to be used (Japanese Unexamined Patent Publication No. S59-125895).

As a method of increasing lysine decarboxylase activity in cells, the lysine decarboxylase activity itself can be increased by introducing a mutation in the structural gene itself of lysine decarboxylase.

As a method of causing a mutation in genes, example include site-specific mutagenesis (Kramer, W. and frita, H. J., Methods in Enzymology, vol. 154, P. 350 (1987)), recombinant PCR (PCR Technology, Stockton Press (1989), a method in which a specific portion of DNA is chemically synthesized, a method in which genes are treated with hydroxyamine, a method in which strain having genes are irradiated with ultraviolet ray, and a method in which strain having genes are treated with chemicals such as nitrosoguanidine or nitrous acid.

The method of culturing such a recombinant cell is not particularly limited, and a known method can be used. To be more specific, for example, when culturing microorganism, as a medium, for example, a medium containing a carbon source, a nitrogen source, and inorganic ions is used.

Examples of carbon sources include saccharides such as glucose, lactose, galactose, fructose, arabinose, maltose, xylose, trehalose, ribose, and hydrolysate of starch; alcohols such as glycerol, mannitol, and sorbitol; and organic acids such as gluconic acid, fumaric acid, citric acid, and succinic acid.

These carbon sources may be used singly or in combination of two or more.

Examples of nitrogen sources include inorganic ammonium salts such as ammonium sulfate, ammonium chloride, and ammonium phosphate; organic nitrogen such as soybean hydrolysate; ammonia gas; and ammonia water.

These nitrogen sources may be used singly or in combination of two or more.

Examples of inorganic ions include sodium ions, magnesium ions, potassium ions, calcium ions, chloride ions, manganese ions, iron ions, phosphoric acid ions, and sulfuric acid ions.

These inorganic ions may be used singly or in combination of two or more.

To the medium, as necessary, other organic components (organic micronutrients) may be added, and examples of such organic components include various amino acids; vitamins such as vitamin $B_1$; required substances of nucleic acids such as RNA; and yeast extracts.

Examples of such a medium include, to be more specific, LB medium.

The cultivation conditions are not particularly limited, and examples thereof include, when cultivating *Escherichia coli*, the following: a cultivation temperature of, for example, 20 to 45° C., preferably 25 to 40° C.; a cultivation pH of, for example, 5.0 to 8.5, preferably 6.5 to 8.0; and culture time of, for example, 12 to 72 hours, preferably 14 to 48 hours. For adjustment of pH, for example, inorganic or organic acidic or alkaline substances, and ammonia gas may be used.

Then, recombinant cells proliferated in such a medium is collected, for example, by centrifugal separation.

In lysine decarboxylation reaction, recombinant cells and/or treated recombinant cells thus obtained, and an aqueous solution of lysine are blended, and allow lysine decarboxylase to act on lysine in water.

The ratio of dry bacterial cell-based weight of bacterial cell (cell) used in the reaction relative to the total weight of lysine used in the reaction is not particularly limited as long as the amount of lysine is sufficient for conversion to 1,5-pentamethylenediamine. For example, the ratio is 0.01 or less, preferably 0.007 or less.

The total weight of lysine used in the reaction is the total of the weight of lysine present in the reaction system at the start of the reaction and the weight of lysine added to the reaction system during the reaction.

The dry bacterial cell-based weight of the bacterial cell is the weight of bacterial cells that are dry and do not contain moisture. The dry bacterial cell-based weight of bacterial cells can be obtained, for example, by separating bacterial cells from a liquid containing bacterial cells (bacterial cell liquid) by a method such as centrifugal separation or filtration, drying the bacterial cells until the weight is a constant weight, and measuring the weight.

The reaction temperature in the lysine decarboxylation is, for example, 28 to 55° C., preferably 35 to 45° C., and the reaction time is, although it is different depending on the type of lysine decarboxylase used, for example, 0.1 to 72 hours, preferably 1 to 72 hours, more preferably 12 to 36 hours. The reaction pH is, for example, 5.0 to 8.5, preferably 5.5 to 8.0.

Lysine is decarboxylated in this manner, and converted to 1,5-pentamethylenediamine.

In this reaction, the obtained 1,5-pentamethylenediamine is alkaline, and therefore the pH of the reaction liquid may increase as lysine is converted to 1,5-pentamethylenediamine. In such a case, as necessary, an acidic substance (e.g., organic acid, and inorganic acid such as hydrochloric acid) can be added to adjust the pH.

The reaction can be conducted under shaking, stirring, or standing conditions.

As the medium of reaction liquid, water, aqueous mediums, organic solvents, or a mixture of water or aqueous mediums and an organic solvent is used. As the aqueous mediums, for example, a buffer solution such as a phosphoric acid buffer solution is used. Any organic solvent that does not inhibit the reaction can be used.

In this reaction, as necessary, for example, vitamin $B_6$ and/or derivatives thereof can be added to the reaction liquid.

Examples of vitamin $B_6$ and/or its derivatives include pyridoxine, pyridoxamine, pyridoxal, and pyridoxal phosphate.

These examples of vitamin $B_6$ and/or its derivatives may be used singly or in combination of two or more.

As the vitamin $B_6$ and/or its derivatives, preferably, pyridoxal phosphate is used.

By adding vitamin $B_6$ and/or its derivatives, production rate and reaction yield of pentamethylenediamine can be improved.

With such a method, by using cells that express lysine decarboxylase treated with an industrially advantageous method, 1,5-pentamethylenediamine can be produced from lysine at high production rate and high reaction yield.

The separation and purification of 1,5-pentamethylenediamine from the reaction liquid can be performed by a method used in general organic synthetic chemistry, for example, by extraction with organic solvents, crystallization, thin-layer chromatography, or high-performance liquid chromatography.

In this method, from the obtained aqueous solution of pentamethylenediamine, as necessary, a portion of water can be distilled off.

To be more specific, for example, the aqueous solution of pentamethylenediamine is heated (heat treatment) using a distillation apparatus etc. equipped with a continuous multiple distillation column, a batch multiple distillation column, etc. under 0.1 kPa to normal pressure, thereby performing distillation. The aqueous solution of pentamethylenediamine in which water is partially distilled off can be obtained in this manner.

The heating temperature is, for example, 25° C. or more and below 90° C., preferably 25° C. or more and 85° C. or less, more preferably 25° C. or more and below 80° C., even more preferably 30° C. or more and 70° C. or less.

When the aqueous solution of pentamethylenediamine is heated (heat treatment) at 90° C. or more, extraction rate of pentamethylenediamine (or its salt) may be reduced.

Also, when the aqueous solution of pentamethylenediamine is heated (heat treatment) at 90° C. or more, and when pentamethylenediamine obtained from the aqueous solution is used to produce pentamethylene diisocyanate, and then produce isocyanate modified substance (described later) from the pentamethylene diisocyanate, reaction rate may be low, and storage stability of the obtained isocyanate modified substance (described later) may be low.

Thus, preferably, without heating (heat treatment) the aqueous solution of pentamethylenediamine at 90° C. or more, more preferably at 80° C. or more, even more preferably without heating (heat treatment) the aqueous solution of pentamethylenediamine, as described later, pentamethylenediamine (or its salt) is extracted from the aqueous solution as is.

In this method, preferably, from the obtained aqueous solution of pentamethylenediamine as described above, pentamethylenediamine (or its salt) is extracted. In the extraction, for example, liquid-liquid extraction method is used.

In the liquid-liquid extraction method, for example, the following methods are used: (1) a method in which by bringing an extractant (described later) into contact with the aqueous solution of pentamethylenediamine batchwise, semi-continuously, or continuously, and mixing and stirring them, pentamethylenediamine (or its salt) is extracted (partitioned) to the extractant (described later), and pentamethylenediamine (or its salt) is separated from the extractant (described later); (2) a method in which an aqueous solution of pentamethylenediamine and an extractant (described later) are supplied countercurrently and continuously to a column (spray column, staged extraction column) equipped with a porous plate, or a column (countercurrent differential extraction column, non-mixing staged extraction column: 5th edition, revised, Chemical Engineers Handbook, p 566 to 569, edited by Society of Chemical Engineers, Maruzen (1988)) equipped with filling, a nozzle, an orifice plate, a baffle, an injector and/or a static mixer, pentamethylenediamine (or its salt) is extracted (partitioned) to the extractant (described later), and thereafter, the extractant (described later) is allowed to flow out continuously, and pentamethylenediamine (or its salt) is separated from the extractant (described later), (3) a method in which an aqueous solution of pentamethylenediamine and an extractant (described later) are supplied countercurrently and continuously to a column (stirring staged extraction column: 5th edition, revised, Chemical Engineers Handbook, p 569 to 574, edited by Society of Chemical Engineers, Maruzen (1988)) equipped with a baffle plate and a stirring blade, pentamethylenediamine (or its salt) is extracted (partitioned) to the extractant (described later), thereafter, the extractant (described later) is allowed to flow out continuously, and pentamethylenediamine (or its salt) is separated from the extractant (described later); and (4) an extractant (described later) is brought into contact with an aqueous solution of pentamethylenediamine using a mixer settler extractor, or a centrifugal extraction apparatus (5th edition, revised, Chemical Engineers Handbook, p 563 to 566, and p 574, edited by Society of Chemical Engineers, Maruzen (1988)), pentamethylenediamine (or its salt) is extracted (partitioned) to the extractant (described later), and pentamethylenediamine (or its salt) is separated from the extractant (described later).

These liquid-liquid extraction methods may be used singly or in combination of two or more.

As the liquid-liquid extraction method, in view of production efficiency, preferably, a method in which pentamethylenediamine (or its salt) is extracted (partitioned) to the extractant (described later) continuously, to be more specific, for example, the above-described methods of (1) to (3) are used.

The mixing ratio of the aqueous solution of pentamethylenediamine to the extractant (described later) in the liquid-liquid extraction is, relative to 100 parts by mass of the aqueous solution of pentamethylenediamine (when the extraction is continuous, supplied amount per unit time. The same is applied below as well.), for example, 30 to 300 parts by mass of the extractant (described later), and in view of economy and productivity, preferably 50 to 200 parts by mass, more preferably 50 to 150 parts by mass, particularly preferably 80 to 120 parts by mass.

In the liquid-liquid extraction, the aqueous solution of pentamethylenediamine and the extractant (described later) are mixed, for example, using stirring blade, etc. under normal pressure (atmospheric pressure), at, for example, 5 to 60° C., preferably, 10 to 60° C., more preferably 15 to 50° C., even more preferably 15 to 40° C., for, for example, 1 to 120 minutes, preferably 5 to 90 minutes, more preferably 5 to 60 minutes.

Examples of stirring blades include, without limitation, for example, propeller, flat blade, flat blade with angles, flat blade with pitch, flat blade disk turbine, blade with tilt disk turbine, bent blade, Pfaudler type stirring blades, blue margin type, dissolver, and anchor.

The number of revolution in the mixing is, for example, 5 to 3000 rpm, preferably 10 to 2000 rpm, more preferably 20 to 1000 rpm.

In this manner, pentamethylenediamine (or its salt) is extracted into the extractant (described later).

Next, in this method, the mixture of pentamethylenediamine (or its salt) and the extractant (described later) is allowed to stand for, for example, 5 to 300 minutes, preferably 10 to 240 minutes, more preferably 20 to 180 minutes, and thereafter, the extractant (pentamethylenediamine extract, that is, a mixture of the extractant (described later) and the pentamethylenediamine (or its salt)) in which pentamethylenediamine (or its salt) is extracted is taken out by a known method.

When the pentamethylenediamine (or its salt) cannot be sufficiently extracted by one liquid-liquid extraction, the liquid-liquid extraction can be conducted repeatedly a plurality of times (e.g., 2 to 5 times).

In this manner, the pentamethylenediamine (or its salt) in the aqueous solution of pentamethylenediamine can be extracted into the extractant (described later).

In the thus obtained extractant (mixture of the extractant (described later) and pentamethylenediamine (or its salt)), the pentamethylenediamine (or its salt) concentration is, for example, 0.2 to 40 mass %, preferably 0.3 to 35 mass %, more preferably 0.4 to 30 mass %, particularly preferably 0.8 to 25 mass %.

The yield (extraction rate) of pentamethylenediamine (or its salt) after the extraction is, based on lysine (or its salt), for example, 65 to 100 mol %, preferably 70 to 100 mol %, more preferably 80 to 100 mol %, particularly preferably 90 to 100 mol %.

In this method, as necessary, for example, pentamethylenediamine (or its salt) can also be isolated from the mixture of the obtained extractant (described later) and pentamethylenediamine (or its salt). The isolation of pentamethylenediamine (or its salt) is not particularly limited, and for example, the isolation of pentamethylenediamine (or its salt) can be performed by distilling the mixture of the extractant (described later) and pentamethylenediamine (or its salt), using a distillation apparatus including a continuous multistage distillation column, a batch multistage distillation column, etc. at, for example, 50 to 182° C., under 0.1 kPa to normal pressure, removing the extractant (described later).

In such an extraction, examples of extractants include non-halogen organic solvents.

The non-halogen organic solvent is an organic solvent that does not contain halogen atoms (fluorine, chlorine, bromine, iodine, etc.) in the molecule, for example, a non-halogen aliphatic organic solvent, a non-halogen alicyclic organic solvent, and a non-halogen aromatic organic solvent.

Examples of non-halogen aliphatic organic solvents include straight chain non-halogen aliphatic organic solvents, and branched non-halogen aliphatic organic solvents.

Examples of straight chain non-halogen aliphatic organic solvents include straight chain non-halogen aliphatic hydrocarbons, straight chain non-halogen aliphatic ethers, and straight chain non-halogen aliphatic alcohols.

Examples of straight chain non-halogen aliphatic hydrocarbons include n-hexane, n-heptane, n-nonane, n-decane, and n-dodecane.

Examples of straight chain non-halogen aliphatic ethers include diethylether, dibutylether, and dihexylether.

Examples of straight chain non-halogen aliphatic alcohols include straight chain monohydric alcohols having 1 to 3 carbon atoms (e.g., methanol, ethanol, n-propanol, isopropanol, etc.), straight chain monohydric alcohols having 4 to 7 carbon atoms (e.g., n-butanol, n-pentanol, n-hexanol, n-heptanol, etc.), and straight chain monohydric alcohols having 8 or more carbon atoms (e.g., n-octanol, n-nonanol, n-decanol, n-undecanol, n-dodecanol etc.).

Examples of branched non-halogen aliphatic organic solvents include branched non-halogen aliphatic hydrocarbons, branched non-halogen aliphatic ethers, branched non-halogen aliphatic monohydric alcohols, and branched non-halogen aliphatic polyhydric alcohols.

Examples of branched non-halogen aliphatic hydrocarbons include 2-methylpentane, 2,2-dimethylbutane, 2,3-dimethylbutane, 2-methylhexane, 3-methylhexane, 2,3-dimethylpentane, 2,4-dimethylpentane, n-octane, 2-methylheptane, 3-methylheptane, 4-methylheptane, 3-ethylhexane, 2,2-dimethylhexane, 2,3-dimethylhexane, 2,4-dimethylhexane, 2,5-dimethylhexane, 3,3-dimethylhexane, 3,4-dimethylhexane, 2-methyl-3-ethylpentane, 3-methyl-3-ethylpentane, 2,3,3-trimethylpentane, 2,3,4-trimethylpentane, 2,2,3,3-tetramethylbutane, and 2,2,5-trimethylhexane.

Examples of branched non-halogen aliphatic ethers include diisopropylether and diisobutylether.

Examples of branched non-halogen aliphatic monohydric alcohols include branched monohydric alcohol having 4 to 7 carbon atoms (e.g., 2-butanol, isobutanol, tert-butanol, 2-pentanol, 3-pentanol, isopentanol, 2-methyl-1-butanol, 2-methyl-3-butanol, 2,2-dimethyl-1-propanol, tert-pentanol, 2-hexanol, 3-hexanol, isohexanol, 2-methyl-2-pentanol, 2-methyl-1-pentanol, 3-methyl-1-pentanol, 2-ethyl-1-butanol, 3,3-dimethyl-1-butanol, 2-heptanol, 3-heptanol, 4-heptanol, 5-methyl-1-hexanol, 4-methyl-1-hexanol, 3-methyl-1-hexanol, 2-ethyl-2-methyl-1-butanol, etc.); and branched monohydric alcohols having 8 or more carbon atoms (e.g., isooctanol, isononanol, isodecanol, 5-ethyl-2-nonanol, trimethylnonylalcohol, 2-hexyldecanol, 3,9-diethyl-6-tridecanol, 2-isoheptylisoundecanol, 2-octyldodecanol, etc.).

Examples of branched non-halogen aliphatic polyhydric alcohols include 2-ethyl-1,3-hexanediol.

These non-halogen aliphatic organic solvents may be used singly or in combination of two or more.

As the non-halogen aliphatic organic solvent, preferably, straight chain non-halogen aliphatic organic solvents, more preferably, straight chain non-halogen aliphatic alcohols are used.

When straight chain non-halogen aliphatic alcohols are used, pentamethylenediamine can be extracted in high yield.

As the non-halogen aliphatic organic solvent, preferably, monohydric alcohols having 4 to 7 carbon atoms (straight chain monohydric alcohol having 4 to 7 carbon atoms, branched monohydric alcohol having 4 to 7 carbon atoms).

When monohydric alcohol having 4 to 7 carbon atoms is used, pentamethylenediamine or its salt can be extracted efficiently, and furthermore, impurity content proportion of pentamethylenediamine or its salt can be decreased.

Examples of non-halogen alicyclic organic solvents include non-halogen alicyclic hydrocarbons (e.g., cyclopentane, methylcyclopentane, cyclohexane, methylcyclohexane, ethylcyclohexane, p-menthane, bicyclohexyl, etc.).

These non-halogen alicyclic organic solvents may be used singly or in combination of two or more.

Examples of non-halogen aromatic organic solvents include non-halogen aromatic hydrocarbons (e.g., benzene, toluene, xylene, ethylbenzene, isopropylbenzene, 1,3,5-trimethylbenzene, 1,2,3,4-tetrahydronaphthalene, n-butylbenzene, sec-butylbenzene, tert-butylbenzene, ethylbenzene, etc.), and phenols (e.g., phenol, cresol, etc.).

These non-halogen aromatic organic solvents may be used singly or in combination of two or more.

Examples of non-halogen organic solvents also include a mixture of aliphatic hydrocarbons and aromatic hydrocarbons, and examples of such a mixture include petroleum ether, and petroleum benzine.

These non-halogen organic solvents may be used singly or in combination of two or more.

As the extractant, in the range that does not inhibit excellent effects of the present invention, for example, halogen organic solvents (organic solvents containing halogen atoms in its molecule) can be used.

Examples of halogen organic solvents include halogen aliphatic hydrocarbons (e.g., chloroform, dichloromethane, carbon tetrachloride, tetrachloroethylene, etc.), halogen aromatic hydrocarbons (e.g., chlorobenzene, dichlorobenzene, chlorotoluene, etc.).

These halogen organic solvents may be used singly or in combination of two or more.

On the other hand, if the halogen organic solvent is used as the extractant, and when pentamethylene diisocyanate (described later) is produced by the obtained pentamethylenediamine or its salt, and further when an isocyanatemodified substance (described later) or a polyurethane resin (described later) is produced by allowing the pentamethylene diisocyanate (described later) to react, productivity and physical property (e.g., yellowing resistance, etc.) of the isocyanate modified substance (described later) may be poor.

Also in the case when a polyurethane resin is produced by allowing such pentamethylene diisocyanate (described later) or an isocyanate modified substance (described later) to react with an active hydrogen compound (described later), physical property (e.g., mechanical strength, chemical resistance, etc.) of the obtained polyurethane resin may be poor.

Therefore, as the extractant, preferably, a non-halogen organic solvent, more preferably, a non-halogen aliphatic organic solvent is used.

When pentamethylenediamine or its salt is extracted by using a non-halogen aliphatic organic solvent, by producing pentamethylene diisocyanate using the obtained pentamethylenediamine or its salt, pentamethylene diisocyanate that is capable of efficient production of an isocyanate modified substance having excellent properties and a polyurethane resin having excellent properties can be produced.

In the present invention, the boiling point of the extractant is, for example, 60 to 250° C., preferably 80 to 200° C., more preferably 90 to 150° C.

When the boiling point of the extractant is below the above-described lower limit, when obtaining pentamethylenediamine or its salt by extraction from the aqueous solution of pentamethylenediamine, separation from the extractant may become difficult.

On the other hand, when the boiling point of the extractant is more than the above-described upper limit, when obtaining pentamethylenediamine or its salt from mixture of the extractant and pentamethylenediamine or its salt, consuming energy at the separation process may increase.

The method of obtaining pentamethylenediamine or its salt from the aqueous solution of pentamethylenediamine is not limited to the above-described extraction, and for example, a known isolation and purification method such as distillation can also be used.

The present invention include 1,5-pentamethylene diisocyanate (hereinafter, may be simply referred to as pentamethylene diisocyanate) produced from the thus obtained 1,5-pentamethylenediamine (or its salt).

Examples of the method of synthesizing 1,5-pentamethylene diisocyanate include a method (hereinafter may be referred to as phosgenation method) in which 1,5-pentamethylenediamine (or its salt) is phosgenated, and a method (hereinafter may be referred to as carbamation method) in which carbamation of 1,5-pentamethylenediamine ((or its salt)) is performed, and thereafter, thermal decomposition is performed.

Examples of the phosgenation method include, to be more specific, a method (hereinafter may be referred to as cold/hot two-stage phosgenation method) in which pentamethylenediamine is allowed to react directly with phosgene, and a method (hereinafter may be referred to as amine hydrochloride phosgenation method) in which hydrochloride of pentamethylenediamine is suspended in an inactive solvent (described later) and then allowed to react with phosgene.

In the cold/hot two-stage phosgenation method, for example, first, an inactive solvent is introduced to a reactor capable of stirring and provided with a phosgene inlet tube, and then the pressure in the reaction system is set to, for example, normal pressure to 1.0 MPa, preferably normal pressure to 0.5 MPa, and the temperature is set to, for example, 0 to 80° C., preferably 0 to 60° C.

Examples of inactive solvents include aromatic hydrocarbons such as benzene, toluene, xylene, ethylbenzene, etc.; aliphatic acid esters such as ethyl acetate, butyl acetate, amyl acetate, etc.; aromatic acid esters such as methyl salicylate, dimethyl phthalate, dibutyl phthalate, methyl benzoate, etc.; chlorinated aromatic hydrocarbons such as monodichlorobenzene, orthodichlorobenzene, trichlorobenzene, etc.; and chlorinated hydrocarbons such as chloroform, carbon tetrachloride, etc.

These inactive solvents may be used singly or in combination of two or more.

The blending amount (total amount) of the inactive solvent relative to 100 parts by mass of pentamethylenediamine as a material is, for example, 400 to 3000 parts by mass, preferably 500 to 2000 parts by mass.

Next, in this method, phosgene is introduced, for example, so that the amount of phosgene is 1 to 10 times mol preferably, 1 to 6 times mol relative to one amino group in pentamethylenediamine; and pentamethylenediamine dissolved in the above-described inactive solvent is added. During this time, the reaction liquid is kept at, for example, 0 to 80° C., preferably, 0 to 60° C., and at the same time, generated hydrogen chloride is released outside of the reaction system via the reflux condenser (cold phosgenation reaction). The contents of the reactor are thus formed into a slurry.

In the cold phosgenation reaction, pentamethylenedicarbamoyl chloride and amine hydrochloride are produced.

Next, in this method, the pressure in the reaction system is set to, for example, normal pressure to 1.0 MPa, preferably 0.05 to 0.5 MPa, and the temperature is increased for, for example, 30 min to 5 hours, to a temperature range of, for example, 80 to 180° C. After the temperature increase, for example, the reaction is allowed to continue for 30 min to 8 hours, thereby dissolving the slurry liquid completely (hot phosgenation reaction).

In the hot phosgenation reaction, at the time of increasing the temperature and the high temperature reaction, the dissolved phosgene is evaporated and escapes outside the reaction system via the reflux condenser, and therefore phosgene is introduced appropriately until the reflux amount from the reflux condenser can be confirmed.

After the termination of the hot phosgenation reaction, an inactive gas such as nitrogen gas is introduced into the reaction system at, for example, 80 to 180° C., preferably 90 to 160° C., thereby purging dissolved excessive phosgene and hydrogen chloride.

In the hot phosgenation reaction, pentamethylenedicarbamoyl chloride produced in the cold phosgenation reaction is thermally decomposed, pentamethylene diisocyanate is produced, and furthermore, amine hydrochloride of pentamethylenediamine is phosgenated, thereby producing pentamethylene diisocyanate.

On the other hand, in the amine hydrochloride phosgenation method, the hydrochloride of pentamethylenediamine is dried sufficiently and finely pulverized, and thereafter, in the same reactor as the reactor of the above-described cold/hot two-stage phosgenation method, hydrochloride of pentamethylenediamine is stirred in the above-described inactive solvent, thereby dispersing the hydrochloride of pentamethylenediamine to form a slurry.

Next, in this method, the reaction temperature is maintained at, for example, 80 to 180° C., preferably 90 to 160° C., and the reaction pressure is maintained at, for example, normal pressure to 1.0 MPa, preferably 0.05 to 0.5 MPa, and phosgene is introduced for 1 to 10 hours so that the total phosgene amount is 1 to 10 times the stoichiometric amount.

Pentamethylene diisocyanate is synthesized in this manner.

The reaction progress can be assumed based on the amount of the hydrogen chloride gas generated, and when the undissolved slurry in the above-described inactive solvent disappeared and the reaction liquid became clear and homogeneous. The generated hydrogen chloride is released, for example, outside the reaction system via the reflux condenser. At the time of reaction termination, the dissolved excessive phosgene and hydrogen chloride are purged by the above-described method. Thereafter, cooling is performed, and the inactive solvent is distilled off under reduced pressure.

Because hydrolyzable chlorine concentration (HC) tends to easily increase in pentamethylene diisocyanate, when using the phosgenation method, and the HC has to be reduced, for example, after the phosgenation reaction and solvent removal, and the pentamethylene diisocyanate that was distilled off is subjected to, for example, heat treatment while allowing an inactive gas such as nitrogen to pass through at, for example, 150° C. to 200° C., preferably 160 to 190° C., for, for example, 1 to 8 hours, preferably 3 to 6 hours. Thereafter, by conducting refining treatment, the HC of pentamethylene diisocyanate can be significantly reduced.

In the present invention, the hydrolyzable chlorine concentration of pentamethylene diisocyanate is, for example, 100 ppm or less, preferably 80 ppm or less, more preferably 60 ppm or less, even more preferably 50 ppm or less.

The hydrolyzable chlorine concentration can be measured, for example, in conformity with the hydrolyzable chlorine testing method described in Annex 3 of JIS K-1556 (2000).

When the hydrolyzable chlorine concentration is more than 100 ppm, the reaction rate of trimerization (described later) is decreased, and may necessitates a large amount of trimerization catalyst (described later), and when a large amount of the trimerization catalyst (described later) is used, the yellowing degree of the obtained polyisocyanate composition (described later) may become high, or the number average molecular weight may increase, which may cause a high viscosity.

When the hydrolyzable chlorine concentration is more than 100 ppm, the viscosity and color may change significantly in the storing process of the polyisocyanate composition (described later) and in the production process of the polyurethane resin (described later).

Examples of carbamation method include urea method.

In the urea method, for example, first, carbamation of pentamethylenediamine is performed, thereby producing pentamethylenedicarbamate (PDC).

To be more specific, as reaction materials, pentamethylenediamine, urea and/or N-non-substitute carbamate, and alcohol are allowed to react with each other.

Examples of N-non-substitute carbamates include N-non-substitute carbamic acid aliphatic esters (e.g., methyl carbamate, ethyl carbamate, propyl carbamate, iso-propyl carbamate, butyl carbamate, iso-butyl carbamate, sec-butyl carbamate, tert-butyl carbamate, pentyl carbamate, iso-pentyl carbamate, sec-pentyl carbamate, hexyl carbamate, heptyl carbamate, octyl carbamate, 2-ethylhexyl carbamate, nonyl carbamate, decyl carbamate, isodecyl carbamate, dodecyl carbamate, tetradecyl carbamate, hexadecyl carbamate, etc.); and N-non-substitute carbamic acid aromatic esters (e.g., phenyl carbamate, tolyl carbamate, xylyl carbamate, biphenyl carbamate, naphthyl carbamate, anthryl carbamate, phenanthryl carbamate, etc.).

These N-non-substitute carbamates may be used singly or in combination of two or more.

As the N-non-substitute carbamate, preferably, N-non-substitute carbamic acid aliphatic esters are used.

Examples of alcohols include primary to tertiary monohydric alcohols, to be more specific, aliphatic alcohols and aromatic alcohols.

Examples of aliphatic alcohols include straight chain aliphatic alcohols (e.g., methanol, ethanol, n-propanol, n-butanol (1-butanol), n-pentanol, n-hexanol, n-heptanol, n-octanol (1-octanol), n-nonanol, n-decanol, n-dodecanol, n-tetradecanol, n-hexadecanol, etc.), and branched aliphatic alcohols (e.g., iso-propanol, iso-butanol, sec-butanol, tert-butanol, iso-pentanol, sec-pentanol, 2-ethylhexanol, iso-decanol, etc.).

Examples of aromatic alcohols include phenol, hydroxytoluene, hydroxyxylene, biphenylalcohol, naphthalenol, anthracenol, and phenanthrol.

These alcohols may be used singly or in combination of two or more.

As the alcohol, preferably, aliphatic alcohols, more preferably straight chain aliphatic alcohols are used.

As the alcohol, preferably, above-described monohydric alcohols having 4 to 7 carbon atoms (straight chain monohydric alcohol having 4 to 7 carbon atoms, and branched monohydric alcohol having 4 to 7 carbon atoms) are used.

Furthermore, when an alcohol (monohydric alcohol having 4 to 7 carbon atoms, etc.) are used as the extractant in the above-described extraction, preferably, the alcohol is used as the reaction material alcohol.

Then, in this method, pentamethylenediamine, urea and/or N-non-substitute carbamate, and alcohol are blended, and preferably, the mixture is allowed to react in the liquid phase.

The mixing ratio of the pentamethylenediamine, urea and/or N-non-substitute carbamate, and alcohol is not particularly limited, and the ratio can be suitably selected in a comparatively wide range.

Usually, the blending amount of urea and N-non-substitute carbamate, and the blending amount of the alcohol equal to or more than the amino group of pentamethylenediamine is sufficient, and therefore urea and/or the above-described N-non-substitute carbamate, and the alcohol itself can also be used as the reaction solvent in this reaction.

When an alcohol (monohydric alcohol having 4 to 7 carbon atoms, etc.) is used in the above-described extraction as the extractant, preferably, the alcohol is used as is as the reaction material and reaction solvent.

When urea and/or the above-described N-non-substitute carbamate, and alcohol are used also as the reaction solvent, as necessary, an excessive amount of urea and/or the above-described N-non-substitute carbamate, or alcohol are used, but with an overly excessive amount, consumption energy in the separation process after the reaction increases, and therefore industrially inappropriate.

Thus, in view of improving the yield of carbamate, the blending amount of urea and/or the above-described N-non-substitute carbamate relative to one amino group of pentamethylenediamine is, 0.5 to 20 times mol, preferably 1 to 10 times mol, more preferably 1 to 5 times mol, and the blending amount of alcohol relative to one amino group of pentamethylenediamine is, 0.5 to 100 times mol, preferably 1 to 20 times mol, more preferably 1 to 10 times mol.

In this method, a catalyst can also be used.

The catalyst is not particularly limited, and examples thereof include: a first group (in conformity with IUPAC Periodic Table of the Elements (version date 22 Jun. 2007). The same applies in the following.) metal compound (e.g., lithium methanolate, lithium ethanolate, lithium propanolato, lithium butanolato, sodium methanolate, potassium-tert-butanolato, etc.), a second group metal compound (e.g., magnesium methanolate, calcium methanolate, etc.), a third group metal compound (e.g., cerium (IV) oxide, uranyl acetate, etc.), a fourth group metal compound (titaniumtetraisopropanolato, titaniumtetrabutanolato, titanium tetrachloride, titaniumtetraphenolate, titanium naphthate, etc.), a fifth group metal compound (e.g., vanadium (III) chloride, vanadium acetylacetonate, etc.), a sixth group metal compound (e.g., chromium (III) chloride, molybdenum (VI) oxide, molybdenum acetyl acetonate, tungsten (VI) oxide, etc.), a seventh group metal compound (e.g., manganous (II) chloride, manganese (II) acetate, manganese (III) acetate, etc.), an eighth group metal compound (e.g., iron (II) acetate, iron (III) acetate, iron phosphate, iron oxalate, ferric (III) chloride, iron (III) bromide, etc.), a ninth group metal compound (e.g., cobalt acetate, cobalt chloride, cobalt sulfurate, cobalt naphthenate, etc.), a tenth group metal compound (e.g., nickel chloride, nickel acetate, nickel naphthenate, etc.), an eleventh group metal compound (e.g., copper (II) acetate, copper (II) sulfate, copper (II) nitrate, bis-(triphenyl-phosphineoxide)-copper (II) chroride, copper molybdate, silver acetate, gold acetate, etc.), a twelfth group metal compound (e.g., zinc oxide, zinc chloride, zinc acetate, zinc acetonyl acetate, zinc octanoate, zinc oxalate, zinc hexylate, zinc benzoate, zinc undecylate, etc.), a thirteen group metal compound (e.g., aluminum acetyl acetonate, aluminum-isobutyrate, aluminum trichloride, etc.), a fourteen group metal compound (e.g., tin (II) chloride, tin (IV) chloride, lead acetate, lead phosphate, etc.), and a fifteenth group metal compound (e.g., antimony (III) chloride, antimony (V) chloride, bismuth (III) chloride, etc.).

Examples of catalysts also include $Zn(OSO_2CF_3)_2$ (also indicated as $Zn(OTf)_2$, zinc trifluoromethanesulfonate), $Zn(OSO_2C_2F_5)_2$, $Zn(OSO_2C_3F_7)_2$, $Zn(OSO_2C_4F_9)_2$, $Zn(OSO_2C_6H_4CH_3)_2$ (zinc p-toluenesulfonate), $Zn(OSO_2C_6H_5)_2$, $Zn(BF_4)_2$, $Zn(PF_6)_2$, $Hf(OTf)_4$ (hafnium trifluoromethanesulfonate, $Sn(OTf)_2$, $Al(OTf)_3$, and $Cu(OTf)_2$.

These catalysts may be used singly or in combination of two or more.

The blending amount of the catalyst relative to 1 mol of pentamethylenediamine is, for example, 0.000001 to 0.1 mol, preferably, 0.00005 to 0.05 mol. When the blending amount of the catalyst is more than such a range, no additional significant reaction facilitating effects can be seen, and at the same time, the increase in the blending amount may increase costs. On the other hand, when the blending amount is smaller than such a range, reaction facilitating effects may not be obtained.

The addition method of the catalyst may be added all at once, continuously, or dividedly and intermittently several times, any of which does not affect reaction activity, and is not limited.

In this reaction, the reaction solvent is not necessarily needed, but when the reaction materials are solid, or when reaction product deposits, for example, a solvent may be blended, which improves handleability.

Examples of solvents is not particularly limited as long as the solvent is inactive or low in reactivity relative to the reaction materials, i.e., pentamethylenediamine, urea and/or N-non-substitute carbamate, and alcohol, and to the reaction product, i.e., a urethane compound, and examples thereof include aliphatic hydrocarbons (e.g., hexane, pentane, petroleum ether, ligroin, cyclododecane, decalin, etc.), aromatic hydrocarbons (e.g., benzene, toluene, xylene, ethylbenzene, isopropylbenzene, butylbenzene, cyclohexylbenzene, tetralin, chlorobenzene, o-dichlorobenzene, methylnaphthalene, chloronaphthalene, dibenzyltoluene, triphenylmethane, phenylnaphthalene, biphenyl, diethylbiphenyl, triethylbiphenyl, etc.), ethers (e.g., diethylether, diisopropylether, dibutylether, anisole, diphenylether, tetrahydrofuran, ethylene glycol dimethyl ether, ethylene glycol diethyl ether, ethylene glycol dibutyl ether, diethylene glycol dimethyl ether, diethylene glycol diethyl ether, etc.), carbonates (e.g., dimethylcarbonate, diethylcarbonate, dipropylcarbonate, dibutylcarbonate, etc.), nitriles (e.g., acetonitrile, propionitrile, adiponitrile, benzonitrile, etc.), aliphatic halogenated hydrocarbons (e.g., methylene chloride, chloroform, 1,2-dichloroethane, 1,2-dichloropropane, 1,4-dichlorobutane, etc.), amides (e.g., dimethylformamide, dimethylacetamide, etc.), nitro compounds (e.g., nitromethane, nitrobenzene, etc.), N-methylpyrrolidinone, N,N-dimethylimidazolidinone, and dimethyl sulfoxide.

Examples of reaction solvents further include the extractants in the above-described extraction.

Of these reaction solvents, in view of economy, and handleability, etc., aliphatic hydrocarbons and aromatic hydrocarbons are used preferably.

Examples of reaction solvents also include, preferably, the extractants in the above-described extraction.

By using the extractant as the reaction solvent, the extracted pentamethylene diisocyanate can be used as is in the carbamation reaction, achieving an improvement in handleability.

Such a reaction solvent may be used singly or in combination of two or more.

The blending amount of the reaction solvent is not particularly limited as long as the amount is an amount that allows the target product, i.e., pentamethylene dicarbamate to dissolve. However, the blending amount of the reaction solvent is preferably small as much as possible because of the following reasons: industrially, the reaction solvent has to be collected from the reaction liquid, and therefore the energy consumed for the collection is to be decreased as much as possible, and also when the blending amount is large, the reaction substrate concentration is decreased and the reaction rate is decreased. To be more specific, the blending amount of the reaction solvent relative to 1 part by mass of pentamethylenediamine is used, usually, in the range of 0.1 to 500 parts by mass, preferably 1 to 100 parts by mass.

In this reaction, the reaction temperature is suitably selected in the range of, for example, 100 to 350° C., preferably 150 to 300° C. When the reaction temperature is lower than the range, the reaction rate may decrease, and when the reaction temperature is higher than the range, side reaction may increase and the yield of the target product, pentamethylene dicarbamate may decrease.

The reaction pressure is usually atmospheric pressure, but when the boiling point of components in the reaction liquid is lower than the reaction temperature, the pressure may be increased, or as necessary, decreased.

The reaction time is, for example, 0.1 to 20 hours, preferably 0.5 to 10 hours. When the reaction time is shorter than such a range, the yield of the target product, i.e., pentamethylene dicarbamate may decrease. On the other hand, the reaction time longer than such a range is inappropriate in view of industrial production.

In the reaction, with the above-described conditions, for example, the reaction vessel is charged with pentamethylenediamine, urea and/or N-non-substitute carbamate, alcohol, and as necessary, a catalyst, and a reaction solvent, and the mixture is stirred or mixed. Then, under mild conditions, pentamethylene dicarbamate is produced in a short period of time for low costs and at high yield.

The obtained pentamethylene dicarbamate corresponds to the above-described pentamethylenediamine, which is usually used as a material component, to be more specific, 1,5-pentamethylene dicarbamate is obtained.

In this reaction, ammonia is produced as a by-product.

In this reaction, when N-non-substitute carbamate is blended, and alcohol corresponding to its ester is produced as a by-product.

In this reaction, the reaction type can be any of batch processing and continuous processing.

In this reaction, preferably, reaction is conducted while ammonia produced as a by-product is discharged. Furthermore, when N-non-substitute carbamate is blended, reaction is conducted while discharging the alcohol produced as a by-product.

In this manner, production of the target product, i.e., pentamethylene dicarbamate is facilitated, and the yield can be further improved/increased.

When the obtained pentamethylene dicarbamate is isolated, for example, pentamethylene dicarbamate may be separated from the reaction liquid including excessive (unreacted) urea and/or N-non-substitute carbamate, excessive (unreacted) alcohol, catalyst, pentamethylene dicarbamate, reaction solvent, ammonia produced as a by-product, alcohol sometimes produced as a by-product, by a known separation refining method.

Then, in the method of producing pentamethylene diisocyanate, the obtained pentamethylene dicarbamate is thermal decomposition, thereby producing pentamethylene diisocyanate.

That is, in such a method of producing isocyanate, the obtained pentamethylene dicarbamate as described above is thermally decomposed, thus producing pentamethylene diisocyanate, and alcohol as a by-product.

The obtained pentamethylene diisocyanate corresponds to the above-described pentamethylenediamine, which is usually used as the material component, to be more specific, 1,5-pentamethylene diisocyanate is obtained.

As the alcohol, usually, alcohol that is the same type with the alcohol used as the material component is produced as a by-product.

The thermal decomposition is not particularly limited, for example, and a known decomposition method such as liquid phase method and gas phase method may be used.

In the gas phase method, pentamethylene diisocyanate and alcohol produced by thermal decomposition can be separated from the gaseous product mixture by fractional condensation. In the liquid phase method, pentamethylene diisocyanate and alcohol produced by thermal decomposition can be separated, for example, by distillation, or by using a solvent and/or an inactive gas as a support substance.

As the thermal decomposition, preferably, in view of workability, liquid phase method is used.

The thermal decomposition reaction of pentamethylene dicarbamate in the liquid phase method is reversible reaction, and thus preferably, in order to suppress reverse reaction (urethane reaction between pentamethylene diisocyanate and alcohol) of thermal decomposition reaction, pentamethylene dicarbamate is subjected to thermal decomposition, and at the same time, pentamethylene diisocyanate, and/or alcohol produced as a by-product are, for example, discharged as gases from the reaction mixture, and then these are separated.

Reaction conditions of thermal decomposition reaction are as follows: preferably, pentamethylene dicarbamate is excellently thermally decomposed; pentamethylene diisocyanate and alcohol produced in the thermal decomposition are evaporated, thereby avoiding equilibrium state of pentamethylene dicarbamate and pentamethylene diisocyanate; and further suppressing side reactions such as polymerization of pentamethylene diisocyanate.

As such reaction conditions, to be more specific, the thermal decomposition temperature is usually 350° C. or less, preferably 80 to 350° C., more preferably, 100 to 300° C. When the thermal decomposition temperature is lower than 80° C., a practical reaction rate may not be obtained, and when the thermal decomposition temperature is more than 350° C., unfavorable side reactions such as polymerization of pentamethylene diisocyanate may be caused. The pressure at the time of thermal decomposition reaction is preferably a pressure that allows the produced alcohol to be evaporated relative to the above-described thermal decomposition reaction temperature, and in view of equipment and application, practically, preferably 0.133 to 90 kPa.

Pentamethylene dicarbamate used in the thermal decomposition may be purified one. Alternatively, using a crude material of pentamethylene dicarbamate obtained by collecting excessive (unreacted) urea and/or N-non-substitute carbamate, excessive (unreacted) alcohol, catalyst, reaction solvent, ammonia produced as a by-product, and alcohol sometimes produced as a by-product after the termination of the above-described reaction (that is, reaction between pentamethylenediamine, urea and/or N-non-substitute carbamate, and alcohol) and separated therefrom, the thermal decomposition may be conducted afterwards.

Furthermore, as necessary, a catalyst and an inactive solvent may be added. These catalyst and inactive solvent may be added, although depending on the types of these, at any of the time of above-described reaction, before and after the distillation separation after the reaction, and before and after the separation of pentamethylene dicarbamate.

As the catalyst used in the thermal decomposition, one or more metal substance selected from Sn, Sb, Fe, Co, Ni, Cu, Zn, Cr, Ti, Pb, Mo, and Mn; or a metal compound such as oxide, halide, carboxylate, phosphate, and an organic metal compound of these used in urethane reaction between isocyanate and hydroxyl groups is used. Of these examples of catalysts, because Fe, Sn, Co, Sb, and Mn exhibit effects of suppressing by-products, they are preferably used.

Examples of metal catalysts of Sn include tin oxide, tin chloride, tin bromide, tin iodide, tin formate, tin acetate, tin oxalate, tin octylate, tin stearate, tin oleate, tin phosphate, dibutyltin dichloride, dibutyltin dilaurate, and 1,1,3,3-tetrabutyl-1,3-dilauryloxydistannoxane.

Examples of metal catalysts of Fe, Co, Sb, and Mn include acetate, benzoate, naphthenate, and acetylacetonato salt thereof.

The blending amount of the catalyst (metal substance or a compound thereof) relative to the reaction liquid is in the range of 0.0001 to 5 mass %, preferably in the range of 0.001 to 1 mass %.

The inactive solvent is not particularly limited, as long as the inactive solvent at least dissolves pentamethylene dicarbamate, is inactive relative to pentamethylene dicarbamate and isocyanate, and is stable at the temperature of thermal decomposition. However, to perform thermal decomposition reaction efficiently, its boiling point is higher than that of the produced isocyanate. Examples of inactive solvents include esters such as dioctyl phthalate, didecyl phthalate, and didodecyl phthalate; and aromatic hydrocarbons and aliphatic hydrocarbons usually used as a heating medium such as dibenzyltoluene, triphenylmethane, phenylnaphthalene, biphenyl, diethylbiphenyl, and triethylbiphenyl.

The inactive solvent can also be obtained from commercially available products, and examples thereof include Barrel process oil B-01 (aromatic hydrocarbons, boiling point: 176° C.), Barrel process oil B-03 (aromatic hydrocarbons, boiling point: 280° C.), Barrel process oil B-04AB (aromatic hydrocarbons, boiling point: 294° C.), Barrel process oil B-05 (aromatic hydrocarbons, boiling point: 302° C.), Barrel process oil B-27 (aromatic hydrocarbons, boiling point: 380° C.), Barrel process oil B-28AN (aromatic hydrocarbons, boiling point: 430° C.), Barrel process oil B-30 (aromatic hydrocarbons, boiling point: 380° C.), Barrel therm 200 (aromatic hydrocarbons, boiling point: 382° C.), Barrel therm 300 (aromatic hydrocarbons, boiling point: 344° C.), Barrel therm 400 (aromatic hydrocarbons, boiling point: 390° C.), Barrel therm 1H (aromatic hydrocarbons, boiling point: 215° C.), Barrel therm 2H (aromatic hydrocarbons, boiling point: 294° C.), Barrel therm 350 (aromatic hydrocarbons, boiling point: 302° C.), Barrel therm 470 (aromatic hydrocarbons, boiling point: 310° C.), Barrel therm PA (aromatic hydrocarbons, boiling point: 176° C.), Barrel therm 330 (aromatic hydrocarbons, boiling point: 257° C.), Barrel therm 430 (aromatic hydrocarbons, boiling point: 291° C.), (all manufactured by Matsumura Oil Co., Ltd.), NeoSK-OIL1400 (aromatic hydrocarbons, boiling point: 391° C.), NeoSK-OIL1300 (aromatic hydrocarbons, boiling point: 291° C.), NeoSK-OIL330 (aromatic hydrocarbons, boiling point: 331° C.), NeoSK-OIL170 (aromatic hydrocarbons, boiling point: 176° C.), NeoSK-OIL240 (aromatic hydrocarbons, boiling point: 244° C.), KSK-OIL260 (aromatic hydrocarbons, boiling point: 266° C.), and KSK-OIL280 (aromatic hydrocarbons, boiling point: 303° C.), (all manufactured by Soken Technix's).

The blending amount of the inactive solvent relative to 1 part by mass of pentamethylene dicarbamate is in the rage of 0.001 to 100 parts by mass, preferably 0.01 to 80 parts by mass, more preferably 0.1 to 50 parts by mass.

The thermal decomposition reaction can be conducted in any of the batch reaction, in which pentamethylene dicarbamate, a catalyst, and an inactive solvent are charged at once, and the continuous reaction, in which pentamethylene dicarbamate is charged in an inactive solvent containing a catalyst under reduced pressure.

In the thermal decomposition, pentamethylene diisocyanate and alcohol are produced, and at the same time, for example, allophanate, amines, urea, carbonate, carbamate, carbon dioxide, etc. may be produced by side reaction, and therefore as necessary, the obtained pentamethylene diisocyanate is refined by a known method.

As the carbamation method, although not to be described in detail, in addition to the above-described urea method, a known carbonation method is also used: that is, a method in which pentamethylene diisocyanate is obtained by synthesizing pentamethylene dicarbamate from pentamethylenediamine, and dialkyl carbonate or diaryl carbonate, and thermally decomposing the pentamethylene dicarbamate in the same manner as described above.

The purity of the thus obtained pentamethylene diisocyanate of the present invention is, for example, 95 to 100 mass %, preferably 97 to 100 mass %, more preferably 98 to 100 mass %, particularly preferably 99 to 100 mass %, most preferably 99.5 to 100 mass %.

To pentamethylene diisocyanate, for example, a stabilizer can also be added.

Examples of stabilizers include antioxidants, acid compounds, compounds containing sulfonamide groups, and organic phosphite.

Examples of antioxidants include hindered phenolic antioxidants, and specific examples include 2,6-di(t-butyl)-4-methylphenol, 2,4,6-tri-t-butylphenol, 2,2'-methylenebis-(4-methyl-6-t-butylphenol), 2,2'-thio-bis-(4-methyl-6-t-butylphenol), 4,4'-thio-bis(3-methyl-6-t-butylphenol), 4,4'-butylidene-bis-(6-t-butyl-3-methylphenol), 4,4'-methylidyne-bis-(2,6-di-t-butylphenol), 2,2'-methylene-bis-[4-methyl-6-(1-methylcyclohexyl)-phenol], tetrakis-[methylene-3-(3,5-di-t-butyl-4-hydroxyphenyl)-propionyl]-methane, 1,3,5-trimethyl-2,4,6-tris-(3,5-di-t-butyl-4-hydroxyphenyl)-propionyl-methane, 1,3,5-trimethyl-2,4,6-tris-(3,5-di-t-butyl-4-hydroxybenzyl)-benzene, N,N-hexamethylene-bis-(3,5-di-t-butyl-4-hydroxyhydrocinnamic acid amide, 1,3,5-tris-(3,5-di-t-butyl-4-hydroxybenzyl)-isocyanurate, 1,1,3-tris-(5-t-butyl-4-hydroxy-2-methylphenyl)-butane, 1,3,5-tris-(3,5-di-t-butyl-4-hydroxybenzyl)-mesitylene, ethylene glycol-bis-[3,3-bis-(3'-t-butyl-4'-hydroxyphenyl)-butyrate, 2,2'-thiodiethyl-bis-3-(3,5-di-t-butyl-4-hydroxyphenyl)-propionate, di-(3-t-butyl-4'-hydroxy-5-methylphenyl)-dicyclopentadiene, 2,2'-methylene-bis-(4-methyl-6-cyclohexylphenol), 1,6-hexanediol-bis-(3,5-di-t-butyl-4-hydroxyphenyl)-propionate, 2,4-bis-(n-octylthio)-6-(4-hydroxy-3,5-di-t-butylanilino)-1,3,5-triazine, diethyl-3,5-di-t-butyl-4-hydroxybenzylphosphonate, triethylene glycol-bis-3-(t-butyl-4-hydroxy-5-methylphenyl)-propionate, and also include, for example, IRGANOX1010, IRGANOX1076, IRGANOX1098, IRGANOX1135, IRGANOX1726, IRGANOX245, IRGANOX3114, and IRGANOX3790 (all manufactured by BASF Japan Ltd., trade name).

These antioxidants may be used singly or in combination of two or more.

Examples of acid compounds include organic acid compounds, to be specific, phosphate, phosphite, hypophosphite, formic acid, acetic acid, propionic acid, hydroxyacetic acid, oxalic acid, lactic acid, citric acid, malic acid, sulfonic acid, sulfonate, phenol, enol, imide, and oxime.

These acid compounds may be used singly or in combination of two or more.

Examples of compounds containing sulfonamide groups include aromatic sulfonamides, and aliphatic sulfonamides.

Examples of aromatic sulfonamides include benzene sulfonamide, dimethylbenzene sulfonamide, sulfanilamide, o- and p-toluene sulfonamide, hydroxynaphthalene sulfonamide, naphthalene-1-sulfonamide, naphthalene-2-sulfonamide, m-nitrobenzene sulfonamide, and p-chlorobenzene sulfonamide.

Examples of aliphatic sulfonamides include methane sulfonamide, N,N-dimethylmethane sulfonamide, N,N-dimethylethane sulfonamide, N,N-diethylmethane sulfonamide, N-methoxymethane sulfonamide, N-dodecylmethane sulfonamide, N-cyclohexyl-1-butanesulfonamide, and 2-aminoethane sulfonamide.

These compounds containing sulfonamide groups may be used singly or in combination of two or more.

Examples of organic phosphites include organic diester phosphonate, and organic triester phosphonate, to be more specific, for example, monophosphites such as triethyl phosphite, tributyl phosphite, tris (2-ethylhexyl) phosphite, tridecyl phosphite, trilauryl phosphite, tris (tridecyl) phosphite, tristearyl phosphite, triphenyl phosphite, tris (nonylphenyl) phosphite, tris (2,4-di-t-butylphenyl) phosphite, diphenyldecyl phosphite, and diphenyl (tridecyl) phosphite; di, tri, or tetra phosphites derived from polyhydric alcohol such as distearyl.pentaerythrityl diphosphite, di.dodecyl.pentaerythritol.diphosphite, di.tridecyl.pentaerythritol.diphosphite, dinonylphenyl.pentaerythritol.diphosphite, tetraphenyl.tetra.tridecyl.pentaerythrityl.tetra phosphite, tetraphenyl.dipropylene glycol.diphosphite, and tripentaerythritol.tri phosphite; and diphosphites derived from bisphenol compounds such as di.alkyl.bisphenol A.diphosphite having 1 to 20 carbons, and 4,4'-butylidene-bis(3-methyl-6-t-butylphenyl-di.tridecyl) phosphite; poly phosphites such as hydrogenated bisphenol A phosphite polymers (molecular weight 2400 to 3000); and tris (2,3-dichloropropyl) phosphite.

These organic phosphites may be used singly or in combination of two or more.

As the stabilizer, preferably, antioxidants, acid compounds, or a compound containing a sulfonamide group is used. More preferably, to pentamethylene diisocyanate, an antioxidant and an acid compound and/or a compound containing a sulfonamide group are blended so that pentamethylene diisocyanate contains these.

By adding these stabilizers, improvement in storage stability of an isocyanate modified substance (described later) obtained by using the pentamethylene diisocyanate can be achieved.

The mixing ratio of the stabilizer is not particularly limited, and is appropriately selected according to necessity and its application.

The mixing ratio of the antioxidant relative to 100 parts by mass of the pentamethylene diisocyanate is, to be specific, for example, 0.0005 to 0.05 parts by mass.

The mixing ratio of the acid compound and/or the compound containing a sulfonamide group (when used in combination, a total of these), relative to 100 parts by mass of pentamethylene diisocyanate, for example, 0.0005 to 0.02 parts by mass.

In the present invention, a polyisocyanate composition is further contained.

The polyisocyanate composition is obtained, to be more specific, by modifying pentamethylene diisocyanate, and contains at least one of the functional group of (a) to (e) below.

(a) an isocyanurate group,
(b) an allophanate group,
(c) a biuret group,
(d) a urethane group, and
(e) a urea group.

The polyisocyanate composition containing the above-described functional group of (a) (isocyanurate group) is a trimer of pentamethylene diisocyanate, and for example, can be obtained by allowing pentamethylene diisocyanate to react in the presence of a known isocyanurate-forming catalyst, thereby allowing trimerization.

The polyisocyanate composition containing the above-described functional group of (b) (allophanate group) is an allophanate-modified substance of pentamethylene diisocyanate, and for example, can be obtained by allowing pentamethylene diisocyanate and a monoalcohol to react, and then further allowing them to react in the presence of a known allophanate-forming catalyst.

The polyisocyanate composition containing the above-described functional group of (c) (biuret group) is a biuret-modified substance of pentamethylene diisocyanate, and for example, can be obtained by allowing pentamethylene diisocyanate to react with, for example, water, tertiary alcohol (e.g., t-butylalcohol, etc.), or secondary amine (e.g., dimethylamine, diethylamine, etc.), and then further allowing them to react in the presence of a known biuretizing catalyst.

The polyisocyanate composition containing the above-described functional group of (d) (urethane group) is a polyol modified substance of pentamethylene diisocyanate, and can be obtained, for example, by reaction between pentamethylene diisocyanate and a polyol component (e.g., trimethylolpropane, etc. described later in detail).

The polyisocyanate composition containing the functional group of above-described (e) (urea group) is a polyamine modified substance of pentamethylene diisocyanate, and can be obtained, for example, by reaction between pentamethylene diisocyanate, and water, or a polyamine component (described later).

The polyisocyanate composition containing at least one of the functional groups of above-described (a) to (e) is sufficient, and can contain two or more of the functional groups of above-described (a) to (e). Such a polyisocyanate composition is produced by suitably combining the above-described reactions.

As the polyisocyanate composition, preferably, a trimer (polyisocyanate composition containing an isocyanurate group) of pentamethylene diisocyanate is used.

Trimer of pentamethylene diisocyanate further includes polyisocyanate having an iminooxadiazinedione group other than the isocyanurate group.

The polyurethane resin of the present invention can be obtained by allowing the above-described pentamethylene diisocyanate, and/or the above-described polyisocyanate composition, and an active hydrogen compound to react with each other.

Examples of active hydrogen compounds include a polyol component (component containing mainly polyol containing two or more hydroxyl groups), and a polyamine component (compound containing mainly polyamine having two or more amino groups).

Examples of polyol component in the present invention include low-molecular-weight polyols and high-molecular weight polyols.

Low-molecular-weight polyols are compounds having two or more hydroxyl groups and a number average molecular weight of below 400, and examples thereof include dihydric alcohols such as ethylene glycol, propylene glycol, 1,3-propanediol, 1,4-butyleneglycol, 1,3-butyleneglycol, 1,2-butyleneglycol, 1,5-pentanediol, 1,6-hexanediol, neopentyl glycol, 3-methyl-1,5-pentanediol, 2,2,2-trimethylpentanediol, 3,3-dimethylolheptane, alkane (C7 to 20) diol, 1,3- or 1,4-cyclohexanedimethanol and a mixture thereof, 1,3- or 1,4-cyclohexanediol and a mixture thereof, hydrogenated bisphenol A, 1,4-dihydroxy-2-butene, 2,6-dimethyl-1-octene-3,8-diol, bisphenol A, diethylene glycol, triethylene glycol, and dipropylene glycol; trihydric alcohols such as glycerin, and trimethylolpropane; tetrahydric alcohols such as tetramethylolmethane (pentaerythritol), and diglycerol; pentahydric alcohol such as xylitol; hexahydric alcohols such as sorbitol, mannitol, allitol, iditol, dulcitol, altritol, inositol, and dipentaerythritol; heptahydric alcohol such as perseitol; and octahydric alcohols such as sucrose.

These low-molecular-weight polyols may be used singly or in combination of two or more.

High-molecular weight polyols are compounds having two or more hydroxyl groups and having a number average molecular weight 400 or more, and examples thereof include polyetherpolyol, polyester polyol, polycarbonate polyol, polyurethane polyol, epoxy polyol, vegetable oil polyol, polyolefin polyol, acrylic polyol, and vinyl monomer-modified polyol.

Examples of polyetherpolyols include polypropylene glycol, and polytetramethylene ether glycol.

Examples of polypropylene glycols include addition polymerized substance (including random and/or block copolymer of two or more alkylene oxides) of alkylene oxides such as ethylene oxide and propylene oxide using the above-described low-molecular-weight polyol or the aromatic/aliphatic polyamine as an initiator.

Examples of polytetramethylene ether glycols include ring-opening polymerized substance obtained by cation polymerization of tetrahydrofuran, and noncrystalline polytetramethylene ether glycol obtained by copolymerizing polymerization unit of tetrahydrofuran and the above-described dihydric alcohol.

Examples of polyester polyols include a polycondensation product obtained by allowing the above-described low-molecular-weight polyol and polybasic acid to react under known conditions.

Examples of polybasic acids include saturated aliphatic dicarboxylic acids (C11 to 13) such as oxalic acid, malonic acid, succinic acid, methylsuccinic acid, glutaric acid, adipic acid, 1,1-dimethyl-1,3-dicarboxypropane, 3-methyl-3-ethylglutaric acid, azelaic acid, sebacic acid, etc.; unsaturated aliphatic dicarboxylic acids such as maleic acid, fumaric acid, itaconic acid, etc.; aromatic dicarboxylic acids such as orthophthalic acid, isophthalic acid, terephthalic acid, toluenedicarboxylic acid, naphthalenedicarboxylic acid, etc.; alicyclic dicarboxylic acids such as hexahydrophthalic acid, etc.; other carboxylic acids such as dimer acid, hydrogenated dimer acid, het acid, etc. and acid anhydrides derived from these carboxylic acids such as oxalic anhydride, succinic anhydride, maleic anhydride, phthalic anhydride, 2-alkyl (C12 to C18) succinic anhydride, tetrahydrophthalic anhydride, trimellitic anhydride, and hallides derived from these carboxylic acids such as oxalyl dichloride, adipoyl dichloride, and sebacoyl dichloride.

Examples of polyester polyols include plants derived polyester polyol, to be specific, vegetable oil polyester polyols obtained by condensation reaction of hydroxycarboxylic acid such as hydroxyl group-containing vegetable oil fatty acid (e.g., castor oil fatty acid containing ricinoleic acid, hydrogenated castor oil fatty acid containing 12-hydroxystearic acid, etc.) using the above-described low-molecular-weight polyol as an initiator under known conditions.

Examples of polyester polyols include polycaprolactone polyol, and polyvalerolactone polyol obtained by ring-opening polymerization of lactones such as ε-caprolactone, γ-valerolactone, etc. and lactides such as L-lactide, D-lactide using the above-described low-molecular-weight polyols (preferably, dihydric alcohol) as an initiator; and further lactone-based polyester polyols obtained by copolymerizing such a polycaprolactone polyol or polyvalerolactone polyol with the above-described dihydric alcohol.

Examples of polycarbonate polyols include ring-opening polymerization substance of ethylene carbonate using the above-described low-molecular-weight polyols (preferably, dihydric alcohol) as an initiator, and noncrystalline polycarbonate polyols obtained by copolymerization of dihydric alcohols such as 1,4-butanediol, 1,5-pentanediol, 3-methyl-1,5-pentanediol, and 1,6-hexanediol with ring-opening polymerization substance.

Polyurethane polyols can be obtained as polyester polyurethane polyol, polyether polyurethane polyol, polycarbonate polyurethane polyol, or polyester polyether polyurethane polyol, by allowing polyester polyol, polyetherpolyol and/or polycarbonate polyol obtained as described above to react with polyisocyanate at an equivalent ratio (OH/NCO) of hydroxyl group (OH) to isocyanate group (NCO) of more than 1.

Examples of epoxy polyols include epoxy polyols obtained by reaction of the above-described low-molecular-weight polyols with polyfunctional halohydrin such as epichlorohydrin, β-methylepichlorohydrin, etc.

Examples of vegetable oil polyols include hydroxyl group-containing vegetable oil such as castor oil, palm oil, etc. Examples thereof include ester-modified castor oil polyol obtained by reaction of castor oil polyol or castor oil fatty acid with polypropylene polyol.

Examples of polyolefin polyols include polybutadiene polyol, and a partially saponified ethylene-vinyl acetate copolymer.

Examples of acrylic polyol include copolymers obtained by copolymerizing hydroxyl group-containing acrylate with a copolymerizable vinyl monomer that is copolymerizable with hydroxyl group-containing acrylate.

Examples of hydroxyl group-containing acrylates include 2-hydroxyethyl (meth)acrylate, hydroxypropyl (meth)acrylate, hydroxybutyl (meth)acrylate, 2,2-dihydroxymethylbutyl (meth)acrylate, polyhydroxyalkylmaleate, and polyhydroxyalkylfumarate. Preferably, 2-hydroxyethyl (meth) acrylate is used.

Examples of copolymerizable vinyl monomers include alkyl (meth)acrylate (1 to 12 carbon atoms) such as methyl (meth)acrylate, ethyl (meth)acrylate, propyl (meth)acrylate, isopropyl (meth)acrylate, butyl (meth)acrylate, isobutyl (meth)acrylate, s-butyl (meth)acrylate, t-butyl (meth)acrylate, pentyl (meth)acrylate, isopentyl (meth)acrylate, hexyl (meth)acrylate, isononyl (meth)acrylate, 2-ethylhexyl (meth) acrylate, and cyclohexylacrylate; aromatic vinyls such as styrene, vinyltoluene, and α-methylstyrene; vinyl cyanide such as (meth) acrylonitrile; vinyl monomers containing carboxyl groups such as (meth) acrylic acid, fumaric acid, maleic acid, and itaconic acid or their alkyl esters; alkanepolyol poly (meth)acrylate such as ethylene glycol di(meth)acrylate, butyleneglycol di(meth)acrylate, hex anediol di(meth)acrylate, oligoethylene glycol di(meth)acrylate, trimethylolpropane di(meth)acrylate, and trimethylolpropanetri (meth) acrylate; and vinyl monomers containing isocyanate groups such as 3-(2-isocyanato-2-propyl)-α-methylstyrene.

Acrylic polyol can be obtained by copolymerizing these hydroxyl group-containing acrylate, and copolymerizable vinyl monomers in the presence of an appropriate solvent and a polymerization initiator.

Examples of acrylic polyol include silicone polyol and fluorine polyol.

Examples of silicone polyols include acrylic polyol in which as the copolymerizable vinyl monomer, for example, a silicone compound containing a vinyl group such as γ-methacryloxypropyltrimethoxysilane is blended in the above-described copolymerization of acrylic polyol.

Examples of fluorine polyols include acrylic polyol in which as the copolymerizable vinyl monomer, for example, a fluorine compound containing a vinyl group such as tetrafluoroethylene, or chlorotrifluoroethylene is blended in the above-described copolymerization of acrylic polyol.

The vinyl monomer-modified polyol can be obtained by allowing the above-described high-molecular weight polyol to react with a vinyl monomer.

As the high-molecular weight polyol, preferably, a high-molecular weight polyol selected from polyetherpolyol, polyester polyol, and polycarbonate polyol.

Examples of vinyl monomers include the above-described alkyl (meth)acrylate, vinyl cyanide, and vinylidene cyanide. These vinyl monomers may be used singly or in combination of two or more. Of these vinyl monomers, preferably, alkyl (meth)acrylate is used.

The vinyl monomer-modified polyol can be obtained by allowing these high-molecular weight polyols to react with vinyl monomers in the presence of, for example, a radical polymerization initiator (e.g., persulfate, organic peroxide, azo compound, etc.).

These high-molecular weight polyols may be used singly or in combination of two or more.

As the high-molecular weight polyol, preferably, polyester polyol, or acrylic polyol is used, more preferably, polyester polyol is used, even more preferably, plant derived polyester polyol is used.

These polyol components may be used singly or in combination of two or more.

Examples of polyamine components include aromatic polyamine, aralkyl polyamine, alicyclic polyamine, aliphatic polyamine, amino alcohol, an alkoxysilyl compound having a primary amino group, or a primary amino group and a secondary amino group, and polyoxyethylene group-containing polyamine.

Examples of aromatic polyamines include 4,4'-diphenylmethanediamine, and tolylenediamine.

Examples of aralkyl polyamine include 1,3- or 1,4-xylylene diamine and mixtures thereof.

Examples of alicyclic polyamines include 3-aminomethyl-3,5,5-trimethylcyclohexylamine (also called: isophoronediamine), 4,4'-dicyclohexylmethanediamine, 2,5(2,6)-bis(aminomethyl)bicyclo[2.2.1]heptane, 1,4-cyclohexanediamine, 1-amino-3-aminomethyl-3,5,5-trimethylcyclohexane, bis-(4-aminocyclohexyl)methane, diaminocyclohexane, 3,9-bis (3-aminopropyl)-2,4,8,10-tetratetraoxaspiro[5.5]undecane, 1,3- and 1,4-bis(aminomethyl)cyclohexane and mixtures thereof.

Examples of aliphatic polyamines include ethylene diamine, propylene diamine, 1,3-propane diamine, 1,4-butanediamine, 1,5-pentanediamine, 1,6-hexamethylenediamine, hydrazine (including hydrate), diethylenetriamine, triethylenetetramine, tetraethylenepentamine, 1,2-diaminoethane, 1,2-diaminopropane, and 1,3-diaminopentane.

Examples of aminoalcohol include N-(2-aminoethyl)ethanolamine.

Examples of alkoxysilyl compound having a primary amino group, or a primary amino group and a secondary amino group include alkoxysilyl group-containing monoamine such as γ-aminopropyltriethoxysilane, and N-phenyl-γ-aminopropyltrimethoxysilane; N-β(aminoethyl)γ-aminopropyltrimethoxysilane; and N-β(aminoethyl)γ-aminopropylmethyldimethoxysilane.

Examples of polyoxyethylene group-containing polyamines include polyoxyalkylene ether diamine such as polyoxyethylene ether diamine. To be more specific, examples thereof include PEG#1000 diamine manufactured by NOF Corporation, Jeffamine ED-2003, EDR-148, and XTJ-512 manufactured by Huntsman Inc.

These polyamine components may be used singly or in combination of two or more.

In the present invention, as necessary, known additives, for example, plasticizers, antiblocking agents, heat-resistant stabilizers, light-resistant stabilizer, antioxidants, release agents, catalysts, as well as pigments, dyes, lubricants, fillers, and hydrolysis inhibitor may be added. These additives may be added at the time of synthesizing components, or may be added at the time of mixing and dissolving components, or may be added after the synthesis.

The polyurethane resin of the present invention can be produced, for example, by polymerization methods such as bulk polymerization and solution polymerization.

In bulk polymerization, for example, under a nitrogen stream, while stirring pentamethylene diisocyanate and/or polyisocyanate composition, an active hydrogen compound is added thereto, and the mixture is allowed to react at a reaction temperature of 50 to 250° C., more preferably at 50 to 200° C., for about 0.5 to 15 hours.

In solution polymerization, pentamethylene diisocyanate and/or polyisocyanate composition, and an active hydrogen compound is added to an organic solvent, and the mixture is allowed to react at a reaction temperature of 50 to 120° C., more preferably at 50 to 100° C., for about 0.5 to 15 hours.

Examples of organic solvents include ketones such as acetone, methyl ethyl ketone, methylisobutylketone, and cyclohexanone; nitriles such as acetonitrile; alkyl esters such as methyl acetate, ethyl acetate, butyl acetate, and isobutyl acetate; aliphatic hydrocarbons such as n-hexane, n-heptane, and octane; alicyclic hydrocarbons such as cyclohexane and methylcyclohexane; aromatic hydrocarbons such as toluene, xylene, and ethylbenzene; glycol ether esters such as methyl cellosolve acetate, ethyl cellosolve acetate, methyl carbitol acetate, ethyl carbitol acetate, ethylene glycol ethylether acetate, propylene glycol methylether acetate, 3-methyl-3-methoxybutyl acetate, and ethyl-3-ethoxypropionate; ethers such as diethylether, tetrahydrofuran, and dioxane; halogenated aliphatic hydrocarbons such as methyl chloride, methylene chloride, chloroform, carbon tetrachloride, methyl bromide, methylene iodide, and dichloroethane; polar aprotic solvents such as N-methylpyrrolidone, dimethylformamide, N,N'-dimethylacetamide, dimethyl sulfoxide, and hexamethyl phosphoramide.

Examples of organic solvents include nonpolar solvents (nonpolar organic solvent), and examples of nonpolar solvents include those nonpolar organic solvents having an aniline point of, for example, 10 to 70° C., preferably 12 to 65° C. and having low toxicity and solvency, such as aliphatic, naphthene hydrocarbon organic solvent; and vegetal oils typically represented by turpentine oil.

The nonpolar organic solvents can be obtained from commercially available products, and examples of those commercially available products include petroleum hydrocarbon organic solvents such as Haws (manufactured by Shell Chemicals, aniline point 15° C.), Swasol 310 (manufactured by Maruzen Petrochemical, aniline point 16° C.), Esso Naphtha No. 6 (manufactured by Exxon Mobil Chemical, aniline point 43° C.), Laws (manufactured by Shell Chemicals, aniline point 43° C.), Esso Naphtha No. 5 (manufactured by Exxon Mobil Corporation, aniline point 55° C.), and pegasol 3040 (manufactured by Exxon Mobil Corporation, aniline point 55° C.); and also turpentine oils such as methylcyclohexane (aniline point 40° C.), ethylcyclohexane (aniline point 44° C.), and gum turpentine N (manufactured by YASUHARA CHEMICAL CO., LTD aniline point 27° C.).

Furthermore, in the above-described polymerization reaction, as necessary, for example, a urethanizing catalyst can be added.

Examples of amines include tertiary amines such as triethylamine, triethylenediamine, bis-(2-dimethylaminoethyl) ether, and N-methylmorpholine; quaternary ammonium salts such as tetraethyl hydroxyl ammonium; and imidazoles such as imidazole and 2-ethyl-4-methylimidazole.

Examples of organic metal compounds include organic tin compounds such as tin acetate, stannous octoate, stannous oleate, tin laurate, dibutyl tin diacetate, dimethyl tin dilaurate, dibutyl tin dilaurate, dibutyl tin dimercaptide, dibutyl tin maleate, dibutyl tin dilaurate, dibutyl tin dineodecanoate, dioctyl tin dimercaptide, dioctyl tin dilaurylate, and dibutyl tin dichloride; organic lead compounds such as lead octanoate and lead naphthenate; organic nickel compound such as nickel naphthenate; organic cobalt compounds such as cobalt naphthenate; organic copper compounds such as octenate copper; organic bismuth compounds such as bismuth octylate and bismuth neodecanoate.

Examples of urethanizing catalysts also include potassium salts such as potassium carbonate, potassium acetate, and potassium octoate.

These urethanizing catalysts may be used singly or in combination of two or more.

In the above-described polymerization reaction, an (unreacted) pentamethylene diisocyanate and/or polyisocyanate composition can be removed, for example, by known removing methods such as distillation and extraction.

In bulk polymerization and solution polymerization, for example, pentamethylene diisocyanate and/or a polyisocyanate composition, and an active hydrogen compound are blended so that the equivalent ratio (NCO/active hydrogen group) of the isocyanate group in the pentamethylene diisocyanate and/or polyisocyanate composition relative to the active hydrogen group (hydroxyl group, amino group) in the active hydrogen compound is, for example, 0.75 to 1.3, preferably, 0.9 to 1.1.

When the above-described polymerization reaction is to be conducted more industrially, the polyurethane resin can be obtained by known methods such as, for example, one-shot method and prepolymer method according to its application. Also, the polyurethane resin can also be obtained by other methods, for example, as an aqueous dispersion (PUD).

In one-shot method, for example, pentamethylene diisocyanate and/or a polyisocyanate composition, and an active hydrogen compound are formulated (mixed) so that the equivalent ratio (NCO/active hydrogen group) of the isocyanate group in the pentamethylene diisocyanate and/or polyisocyanate composition relative to the active hydrogen group (hydroxyl group, amino group) in the active hydrogen compound is, for example, 0.75 to 1.3, preferably 0.9 to 1.1, and then thereafter, the mixture is allowed to react (curing reaction), for example, at room temperature to 250° C., preferably at room temperature to 200° C., for, for example, 5 minutes to 72 hours, preferably 4 to 24 hours. The curing temperature may be a constant temperature, or may be increased/decreased stepwise.

In prepolymer method, for example, first, pentamethylene diisocyanate and/or a polyisocyanate composition, and a portion of an active hydrogen compound (preferably, high-molecular weight polyol) are allowed to react, thereby synthesizing an isocyanate group-terminated prepolymer having isocyanate groups at its molecular terminals. Then, the obtained isocyanate group-terminated prepolymer is allowed to react with the remaining portion of the active hydrogen compound (preferably, low-molecular-weight polyol and/or polyamine component), thereby causing curing reaction. In the prepolymer method, the remaining portion of the active hydrogen compound is used as a chain extender.

To synthesize the isocyanate group-terminated prepolymer, pentamethylene diisocyanate and/or polyisocyanate composition, and a portion of the active hydrogen compound are formulated (mixed) so that the equivalent ratio (NCO/active hydrogen group) of the isocyanate group in the pentamethylene diisocyanate and/or polyisocyanate composition relative to the active hydrogen group in the portion of the active hydrogen compound is, for example, 1.1 to 20, preferably 1.3 to 10, more preferably 1.3 to 6, and then the mixture is allowed to react in the reaction vessel, for example, at room temperature to 150° C., preferably at 50 to 120° C., at for example, 0.5 to 18 hours, preferably 2 to 10 hours. In this reaction, as necessary, the above-described urethanizing catalyst may be added, and after the completion of reaction, as necessary, the unreacted pentamethylene diisocyanate and/or polyisocyanate composition can be removed, for example, by a known removal method such as distillation or extraction.

Then, to cause the reaction between the obtained isocyanate group-terminated prepolymer and the remaining portion of the active hydrogen compound, the isocyanate group-terminated prepolymer and the remaining portion of the active hydrogen compound are formulated (mixed) so that the equivalent ratio (NCO/active hydrogen group) of the isocyanate group in the isocyanate group-terminated prepolymer relative to the active hydrogen group in the remaining portion of the active hydrogen compound is, for example, 0.75 to 1.3, preferably 0.9 to 1.1, and the mixture is allowed to react (curing reaction), for example, at room temperature to 250° C., preferably at room temperature to 200° C., for, for example, 5 minutes to 72 hours, preferably 1 to 24 hours.

To obtain the polyurethane resin as a aqueous dispersion, for example, first, pentamethylene diisocyanate and/or a polyisocyanate composition are/is allowed to react with an active hydrogen compound including an active hydrogen compound (hereinafter abbreviated as a hydrophilic group-containing active hydrogen compound) containing a hydrophilic group to be described later, thereby producing an isocyanate group-terminated prepolymer.

Then, the obtained isocyanate group-terminated prepolymer is allowed to react with a chain extender in water, thereby causing them to disperse. In this manner, an aqueous polyurethane resin in which chains of an isocyanate group-terminated prepolymer are extended by a chain extender can be obtained as an internally emulsified aqueous dispersion.

To cause the isocyanate group-terminated prepolymer to react with the chain extender in water, for example, first, the isocyanate group-terminated prepolymer is added to water, thereby dispersing the isocyanate group-terminated prepolymer. Thereafter, a chain extender is added thereto, thereby causing chains of the isocyanate group-terminated prepolymer to extend.

The hydrophilic group-containing active hydrogen compound is a compound having both of a hydrophilic group and an active hydrogen group, and examples of hydrophilic groups include anionic groups (e.g., carboxyl group, etc.), cationic groups, and nonionic group (e.g., polyoxyethylene group, etc.). Examples of hydrophilic group-containing active hydrogen compounds include, to be more specific, carboxylic acid group-containing active hydrogen compounds, and polyoxyethylene group-containing active hydrogen compounds.

Examples of carboxylic acid group-containing active hydrogen compounds include dihydroxylcarboxylic acids such as 2,2-dimethylolacetic acid, 2,2-dimethylollactic acid, 2,2-dimethylol propionic acid, 2,2-dimethylolbutanoic acid, 2,2-dimethylolbutyric acid, and 2,2-dimethylolvaleric acid; diaminocarboxylic acids such as lysine, and arginine; metal salts thereof; and ammonium salts thereof.

The polyoxyethylene group-containing active hydrogen compound is a compound containing a polyoxyethylene group at its main chain or a side chain and having two or more active hydrogen groups, and examples thereof include polyethylene glycol, and polyoxyethylene side chain-containing polyol (a compound containing a polyoxyethylene group at its side chain, and having two or more active hydrogen groups).

These hydrophilic group-containing active hydrogen compounds may be used singly or in combination of two or more.

As the chain extender, for example, low-molecular-weight polyols such as the above-described dihydric alcohol, and the above-described trihydric alcohol; and diamines such as alicyclic diamines and aliphatic diamines may be used.

These chain extenders may be used singly or in combination of two or more.

When an active hydrogen compound containing a hydrophilic group-containing active hydrogen compound is used as described above, as necessary, the hydrophilic group is neutralized by a known neutralizing agent.

When the hydrophilic group-containing active hydrogen compound is not used as the active hydrogen compound, the polyurethane resin can be obtained as an externally emulsified aqueous dispersion by emulsification, for example, using a known surfactant.

Such 1,5-pentamethylene diisocyanate, a polyisocyanate composition, and a polyurethane resin are produced by using 1,5-pentamethylenediamine obtained at high production rates and high reaction yield as a material, and therefore can be obtained at high production rates and high reaction yield.

EXAMPLES

In the following, Examples of the present invention will be described, but the present invention is not limited thereto. L-lysine and 1,5-pentamethylenediamine are determined by high-performance liquid chromatography (HPLC). Analysis conditions of these and measurement method of lysine decarboxylase activity are shown below.

<Analysis Conditions of L-lysine and 1,5-pentamethylenediamine>

Column; Asahipak ODP-50 4E (manufactured by Showa Denko K.K.)

Column Temperature; 40° C.
Eluent; 0.2M sodium phosphate (pH7.7)+2.3 mM sodium 1-octanesulfonate
Eluent Flow Rate; 0.5 mL/min For detection, postcolumn derivatization [J. Chromatogr., 83, 353-355 (1973)] using o-phthalaldehyde is used.

<Reaction Yield of 1,5-pentamethylenediamine (Unit: Mol %)>

Using L-lysine monohydrochloride (manufactured by Wako Pure Chemical Industries, Ltd.) and 1,5-pentamethylenediamine dihydrochloride (manufactured by Tokyo Chemical Industry), L-lysine and 1,5-pentamethylenediamine concentrations based on the calibration curve made from the area value of the chromatograph obtained under the above-described HPLC analysis conditions were calculated, and the ratio of the 1,5-pentamethylenediamine concentration relative to the total concentration of L-lysine and 1,5-pentamethylenediamine was regarded as reaction yield of 1,5-pentamethylenediamine.

<Measurement Method of Lysine Decarboxylase Activity>

To 200 mM of sodium phosphate buffer solution (pH7.0) containing 200 mM of L-lysine monohydrochloride and 0.15 mM of pyridoxal phosphate (manufactured by Hiroshima Wako Ltd.), a bacterial cell suspension or a treated bacterial cell suspension was added, thereby preparing a total mixture of 0.2 mL, and the mixture was allowed to react at 37° C. for 6 minutes. To the reaction liquid, 1 mL of hydrochloric acid (0.2M) was added, thereby terminating the reaction. The reaction terminated liquid was diluted with water appropriately, and the produced 1,5-pentamethylenediamine was determined by HPLC.

The activity unit was set so that 1 unit represents activity of producing 1 μmol of 1,5-pentamethylenediamine in 1 minute.

<Purity of Pentamethylenediamine (Unit: Mass %)>

Using purified pentamethylenediamine obtained in (distillation of pentamethylenediamine) to be described later, purity of pentamethylenediamine was calculated based on calibration curve made from the area value of a gas chromatogram obtained under the following gas chromatograph analysis conditions.

Apparatus; GC-6890 (manufactured by Agilent)
Column; WCOT FUSED SILICA CP-SIL 8CB FOR AMINES (manufactured by VARIAN)
Oven temperature; held at 40° C. for 3 minutes, temperature increased at 10° C./min from 40° C. to 300° C., and held at 300° C. for 11 minute
Inlet Temperature; 250° C.
Detector temperature; 280° C.
Carrier Gas; helium
Detection Method; FID <Extraction Rate (Unit: Mass %)>

To obtain extraction rate of pentamethylenediamine using an extractant, the above-described measurement (purity of pentamethylenediamine) was conducted, and the pentamethylenediamine concentration in the aqueous solution of pentamethylenediamine before the extraction operation, and the pentamethylenediamine concentration in the extractant after the extraction operation were measured.

Then, the extraction rate was calculated based on the following formula.

mass of pentamethylenediamine in extractant=pentamethylenediamine concentration in extractant×mass of extractant/100 (a)

mass of pentamethylenediamine in charged aqueous solution of pentamethylenediamine=diaminopentane concentration in aqueous solution of pentamethylenediamine before extraction operation×mass of charged aqueous solution of pentamethylenediamine/100 (b)

extraction rate (mass %)=$(a)/(b) \times 100$

<Purity of Pentamethylene Diisocyanate (Unit: Mass %)>

The purity of pentamethylene diisocyanate was measured using a potential difference titrator in conformity with JIS K-1556 based on the isocyanate group concentration measured by n-dibutylamine method.

<Pentamethylene Diisocyanate Concentration (Unit: Mass %)>

Using pentamethylene diisocyanate (a) obtained in Example 17 to be described later, the pentamethylene diisocyanate concentration in the polyisocyanate composition was calculated based on calibration curve made from the area value of chromatogram obtained under the following HPLC analysis conditions.

Apparatus; Prominence (manufactured by Shimadzu Corporation)
1) Pump LC-20AT
2) Degasser DGU-20A3
3) Autosampler SIL-20A
4) Column constant temperature bath COT-20A
5) Detector SPD-20A
Column; SHISEIDO SILICA SG-120
Column Temperature; 40° C.
Fluent; n-hexane/methanol/1,2-dichloroethane=90/5/5 (Volume Ratio)
Flow Rate; 0.2 mL/min
Detection method; UV 225 nm <Purity of bis(butoxycarbonylamino)pentane (Unit: Mass %)>

The purity of bis(butoxycarbonylamino)pentane was calculated based on the calibration curve made from the area value of chromatogram obtained under the following HPLC analysis conditions.

Apparatus; alliance 2695 separation module (manufactured by Waters)
Detector 2414 RI Detector
Column; Unison UK C-18 manufactured by Imtakt
Column Temperature; 40° C.
Eluent; acetonitrile/distilled water=45/55 (volume ratio)
Flow Rate; 1.0 mL/min
Detection method; RI <Yield of bis(butoxycarbonylamino)pentane (Unit: Mass %>

Yield of bis(butoxycarbonylamino)pentane was calculated using the formula below.

$$(W_2 \times C_2/100)/(W_1 \times C_1/100 \times M_2/M_1) \times 100$$

$M_1$: molecular weight of pentamethylenediamine
$M_2$: molecular weight of bis(butoxycarbonylamino)pentane
$C_1$: pentamethylenediamine concentration in n-butanol solution
$C_2$: purity of bis(butoxycarbonylamino)pentane
$W_1$: parts by mass of charged solution of pentamethylenediamine in n-butanol
$W_2$: parts by mass of the obtained bis(butoxycarbonylamino)pentane <Purity of Pentamethylene Diisocyanate (Unit: Mass %)>

The purity of pentamethylene diisocyanate was measured using a potential difference titrator by n-dibutylamine method in conformity with JIS K-1603-1.

<Yield of Thermal Decomposition Reaction (Unit: Mass %)>
Yield of thermal decomposition reaction was calculated using the formula below.

$$(W_4 \times C_3/100)/(W_3 \times C_2/100 \times M_3/M_2) \times 100$$

$M_3$: Molecular Weight of Pentamethylene Diisocyanate
$C_3$: Purity of Pentamethylene Diisocyanate
$W_3$: parts by mass of charged bis(butoxycarbonylamino)pentane
$W_4$: parts by mass of obtained pentamethylene diisocyanate <Yield of Pentamethylene Diisocyanate (Unit: Mass %)>
The yield of pentamethylene diisocyanate was calculated using the formula below.

$$A \times B/100$$

A: yield of bis(butoxycarbonylamino)pentane
B: yield of thermal decomposition reaction <Conversion Rate of Isocyanate Group (Unit: %)>
The conversion rate of isocyanate group is determined as follows: in the chromatogram obtained under the following GPC measurement conditions, the proportion of the peak area on the high-molecular weight-side than the peak of pentamethylene diisocyanate relative to the total peak area was regarded as the conversion rate of isocyanate group.

Apparatus; HLC-8020 (manufactured by Tosoh Corporation)
Column; G1000HXL, G2000HXL and G3000HXL (all manufactured by TOSOH CORPORATION, trade names) are connected in series
Column Temperature; 40° C.
Eluent; tetrahydrofuran
Flow Rate; 0.8 mL/min
Detection method; differential refractive index
Standard Substance; polyethylene oxide (manufactured by Tosoh Corporation, trade name: TSK standard polyethylene oxide)

<Isocyanate Trimer Concentration (Unit: Mass %)>
The measurement described above of (conversion rate of isocyanate group) was conducted, and the peak area proportion corresponding to three times the molecular weight of pentamethylene diisocyanate, regarded as the isocyanate trimer concentration.

<Isocyanate Group Concentration (Unit: Mass %)>
The isocyanate group concentration of the polyisocyanate composition was measured by n-dibutylamine method in conformity with JIS K-1556 using a potential difference titrator.

<Viscosity (Unit: mPa·s)>
Using an E-type viscometer TV-30 manufactured by TOKI Sangyo Co., Ltd., the viscosity of the polyisocyanate composition at 25° C. was measured.

<Color (Unit: APHA)>
The color of the polyisocyanate composition was measured by the method in conformity with JIS K-0071.

(Distillation of Pentamethylenediamine)
A four-neck flask equipped with a thermometer, a distillation column, a condenser tube, and a nitrogen inlet tube was charged with pentamethylenediamine (manufactured by TOKYO CHEMICAL INDUSTRY CO., LTD.), and under conditions of a column top temperature of 111 to 115° C. and 10 KPa, the pentamethylenediamine was rectified while further being refluxed, thereby producing a refined pentamethylenediamine. The pentamethylenediamine subjected to the distillation refined had an area proportion in gas chromatography of 100%.

Example 1

[Cloning of Lysine Decarboxylase Gene (cadA)]
A genomic DNA prepared from *Escherichia coli* W3110 strain (ATCC27325) in accordance with a common procedure was used as a template for PCR.

As the primer for PCR, oligonucleotide (synthesized by Invitrogen Corporation by request) having a base sequence shown in sequence ID Nos. 1 and 2 designed based on the base sequence of lysine decarboxylase gene (cadA) (GenBank Accession No. AP009048) was used. These primers have restriction enzyme recognition sequences of KpnI and XbaI in the proximity of 5'-end.

Using 25 μL of a PCR reaction liquid containing 1 ng/μL of the genomic DNA and 0.5 pmol/μL each of the primers, a PCR was conducted for 30 cycles under the following conditions: a reaction cycle of denaturation: 94° C., 30 seconds, annealing: 55° C., 30 minutes, and extension reaction: 68° C., 2 minutes.

PCR reaction product and plasmid pUC18 (manufactured by Takara Shuzo Co., Ltd.) were digested with KpnI and XbaI, and ligated using Ligation high (manufactured by TOYOBO CO., LTD.). Thereafter, using the obtained recombinant plasmid, *Escherichia coli* DH5α (manufactured by TOYOBO CO., LTD.) was transformed. The transformant was cultured in LB agar medium containing ampicillin (Am) 100 μg/mLb and X-Gal (5-bromo-4-chloro-3-indolyl-β-D-galactoside), thereby producing an Am-resistant, white colony transformant. The plasmid was extracted from the thus obtained transformant.

It was confirmed that the base sequence of the DNA fragment inserted into the plasmid was the base sequence shown in sequence ID No. 3 according to a common base sequence determination method.

The obtained plasmid having a DNA that codes lysine decarboxylase was named pCADA. By culturing *Escherichia coli* transformed using pCADA, lysine decarboxylase having amino acid sequence shown in sequence ID No. 4 could be produced.

[Preparation of Transformant]
*Escherichia coli* W3110 strain was transformed by a usual method using pCADA, and the obtained transformant was named W/pCADA.

The transformant was inoculated into 500 ml of LB medium containing Am 100 μg/mL in a 2 L Erlenmeyer flask having a baffle, and cultured with shaking at 30° C. until OD (660 nm) reached 0.5; thereafter, IPTG (isopropyl-β-thiogalactopyranoside) was added thereto so that the IPTG was 0.1 mM therein, and shaking culture was conducted for further 14 hours. The culture solution was subjected to centrifugal separation at 8000 rpm (maximum centrifugal acceleration 10800×g) for 20 min, thereby collecting bacterial cells. The collected bacterial cell had a concentration based on dry bacterial cell of 25 mass %. The dry bacterial cell-based concentration was obtained by using a portion of the collected bacterial cell, dried until its weight reached a constant weight, and measuring the weight before and after the drying.

Examples 2 and 3, and Comparative Examples 1 and 2

[Effects of Dry Bacterial Cell-Based Concentration in Heat Treatment]
The collected bacterial cell of transformant W/pCADA obtained in Example 1 was suspended in water, thereby preparing bacterial cell suspensions having dry bacterial cell-based concentrations shown in Table 1. These bacterial cell suspensions were incubated in a warm water bath of a temperature of 60° C. for 30 minutes, thereby giving a heat treatment. The bacterial cell suspension after the heat treatment was suitably diluted with a diluent (10 mM of a sodium phosphate buffer solution (pH7.0) containing 0.15 mM pyridoxal phosphate and 5 g/L bovine albumin (manufactured by SIGMA)), and measurement of lysine decarboxylase activity was conducted using the obtained bacterial cell diluted solution. In Comparative Example 1, the collected bacterial cell of transformant W/pCADA obtained in Example 1 was suitably suspended as is with a diluent, and measurement of enzyme activity was conducted using the bacterial cell diluted solution without heat treatment. The results are shown in Table 1.

TABLE 1

| Nos. of Comp. Ex. and Ex. | Dry bacterial cell-based concentration At the time of heat treatment | Bacterial Cell Activity | Relative Activity |
|---|---|---|---|
| Comp. Ex. 1 | (without heat treatment) | 1.44 | 1.00 |
| Ex. 2-1 | 13 mass % | 100.6 | 70.1 |
| Ex. 2-2 | 0.026 mass % | 23.7 | 16.5 |

The bacterial cell activity is indicated as the enzyme activity (U/mg dry cells) per 1 mg of dry bacterial cell-based weight. The relative activity is indicated setting the bacterial cell activity of Comparative Example 1 as 1.

The above-described bacterial cell diluted solutions were disrupted for 5 minutes in ice water using Bioruptor (manufactured by Olympus Corporation), and measurement of lysine decarboxylase activity was conducted using the obtained bacterial cell-disrupted solution. The results are shown in Table 2.

TABLE 2

| Nos. of Comp. Ex. and Ex. | Dry bacterial cell-based concentration At the time of heat treatment | Bacterial Cell Activity | Relative Activity |
|---|---|---|---|
| Comp. Ex. 2 | (without heat treatment) | 106.0 | 1.00 |
| Ex. 3-1 | 13 mass % | 108.7 | 1.03 |
| Ex. 3-2 | 0.026 mass % | 31.2 | 0.29 |

The bacterial cell activity is indicated as the enzyme activity (U/mg dry cells) per 1 mg of dry bacterial cell-based weight. The relative activity is indicated setting the bacterial cell activity of Comparative Example 2 as 1. The relative activity indicates lysine decarboxylase activity remaining rate after heat treatment.

The results of Table 1 showed that bacterial cell activity improved by setting dry bacterial cell-based concentration of the bacterial cell suspension to 0.026 mass % or more in the heat treatment. On the other hand, the results of Table 2 showed that by setting the dry bacterial cell-based concentration to 13 mass %, the activity remaining rate was about 100%, and lysine decarboxylase showed high stability.

Example 4

[Effects of Heat Treatment 1]
The collected bacterial cell of the transformant W/pCADA obtained in Example 1 was suspended in water, and a bacterial cell suspension having a dry bacterial cell-based concentration of 12.5 mass % was prepared. The bacterial cell suspension was incubated in a warm water bath having temperatures shown in Table 3 for 15 minutes, 30 minutes, and 60 minutes, thereby giving a heat treatment. The bacterial cell suspension after the heat treatment was suitably diluted with a diluent (10 mM of a sodium phosphate buffer solution (pH7.0) containing a 0.15 mM pyridoxal phosphate and 5 g/L bovine albumin (manufactured by SIGMA)), and measurement of lysine decarboxylase activity was conducted using the obtained bacterial cell diluted solution. The results are shown in Table 3. In Comparative Example, the results when using untreated bacterial cells of Comparative Example 1 are shown.

TABLE 3

| Nos. of Comp. Ex. and Ex. | Heat Treatment Temperature | Heat Treatment Time | Bacterial Cell Activity | Relative Activity |
|---|---|---|---|---|
| Comp. Ex. 1 | (without heat treatment) | — | 1.44 | 1.00 |
| Ex. 4-1 | 40° C. | 15 minutes | 1.42 | 0.99 |
|  |  | 30 minutes | 1.43 | 1.00 |
|  |  | 60 minutes | 1.45 | 1.01 |
| Ex. 4-2 | 50° C. | 15 minutes | 3.09 | 2.15 |
|  |  | 30 minutes | 8.14 | 5.67 |
|  |  | 60 minutes | 15.8 | 11.0 |
| Ex. 4-3 | 60° C. | 15 minutes | 93.0 | 64.7 |
|  |  | 30 minutes | 100.6 | 70.1 |
|  |  | 60 minutes | 99.7 | 69.4 |
| Ex. 4-4 | 70° C. | 15 minutes | 79.8 | 55.6 |
|  |  | 30 minutes | 38.0 | 26.5 |
|  |  | 60 minutes | 16.1 | 11.2 |
| Ex. 4-5 | 80° C. | 15 minutes | Not Detected | 0 |
|  |  | 30 minutes | Not Detected | 0 |
|  |  | 60 minutes | Not Detected | 0 |

The bacterial cell activity is indicated as the enzyme activity (U/mg dry cells) per 1 mg of dry bacterial cell-based weight. The relative activity is indicated setting the bacterial cell activity of Comparative Example 1 as 1.

By conducting heat treatment of from 50° C. to 70° C., bacterial cell activity improved.

Example 5

[Stability of Lysine Decarboxylase in Heat Treatment]
The bacterial cell diluted solution after heat treatment obtained in Example 4 and the bacterial cell diluted solution obtained in Comparative Example 1 were disrupted for 5 minutes in ice water using Bioruptor (manufactured by Olympus Corporation), and measurement of lysine decarboxylase activity was conducted using the obtained bacterial cell-disrupted solution. The results are shown in Table 4.

TABLE 4

| Nos. of Comp. Ex. and Ex. | Heat Treatment Temperature | Heat Treatment Time | Bacterial Cell Activity | Relative Activity |
|---|---|---|---|---|
| Comp. Ex. 2 | (without heat treatment) | — | 106.0 | 1.00 |
| Ex. 5-1 | 40° C. | 15 minutes | 108.1 | 1.02 |
|  |  | 30 minutes | 102.2 | 0.96 |
|  |  | 60 minutes | 105.0 | 0.99 |
| Ex. 5-2 | 50° C. | 15 minutes | 108.1 | 1.02 |
|  |  | 30 minutes | 108.7 | 1.03 |
|  |  | 60 minutes | 107.5 | 1.01 |
| Ex. 5-3 | 60° C. | 15 minutes | 107.0 | 1.01 |
|  |  | 30 minutes | 108.7 | 1.03 |
|  |  | 60 minutes | 101.3 | 0.96 |

TABLE 4-continued

| Nos. of Comp. Ex. and Ex. | Heat Treatment Temperature | Heat Treatment Time | Bacterial Cell Activity | Relative Activity |
|---|---|---|---|---|
| Ex. 5-4 | 70° C. | 15 minutes | 74.1 | 0.70 |
| | | 30 minutes | 35.7 | 0.34 |
| | | 60 minutes | 15.5 | 0.15 |
| Ex. 5-5 | 80° C. | 15 minutes | Not Detected | 0 |
| | | 30 minutes | Not Detected | 0 |
| | | 60 minutes | Not Detected | 0 |

The bacterial cell activity is indicated as the enzyme activity (U/mg dry cells) per 1 mg of dry bacterial cell-based weight. The relative activity is indicated setting the bacterial cell activity of Comparative Example 2 as 1. The relative activity indicates lysine decarboxylase activity remaining rate after heat treatment.

In the heat treatment, with a treatment temperature of 60° C. or less and a treatment time of within 60 minutes, activity remaining rate was 96% or more, and lysine decarboxylase had high stability. Even with a treatment temperature of 70° C., up to the treatment time of 15 minutes, lysine decarboxylase showed high stability with the activity remaining rate of 70° A or more.

Example 6

[Effects of Heat Treatment 2]

To a 300 mL flask, 120 g of a substrate solution was added: the substrate solution was prepared so that the final concentration of L-lysine monohydrochloride was 10 mass % and the final concentration of pyridoxal phosphate was 0.15 mM. Then, heat-treated bacterial cells (dry bacterial cell-based weight 0.0144 g) prepared in Example 4 with a heat treatment at a temperature of 60° C., a time of 30 minutes or untreated bacterial cells (dry bacterial cell-based weight 0.0144 g) of Comparative Example 1 were added thereto, thereby allowing the reaction to start. The reaction conditions were as follows: 37° C. and 200 rpm. The reaction results are shown in Table 5 and FIG. 1.

TABLE 5

| | Reaction Yield(mol %) | |
|---|---|---|
| Reaction Time | Untreated Bacterial Cells | 60° C. Heat-treated Bacterial Cells |
| 1 hour | 3.9 | 56.7 |
| 2 hours | 8.4 | 81.9 |
| 3 hours | 15.7 | 92.6 |
| 5 hours | 31.1 | 97.0 |
| 21 hours | 81.9 | 99.0 |
| 24 hours | 83.6 | 99.0 |

While the untreated bacterial cells resulted in the yield of 83.6 mol % with a reaction of 24 hours, the 60° C. heat-treated bacterial cells resulted in the yield of 99.0 mol % with a reaction of 24 hours, i.e., the reactivity improved.

Example 7

[Effects of Lysine Hydrochloride Treatment]

Figure 2:
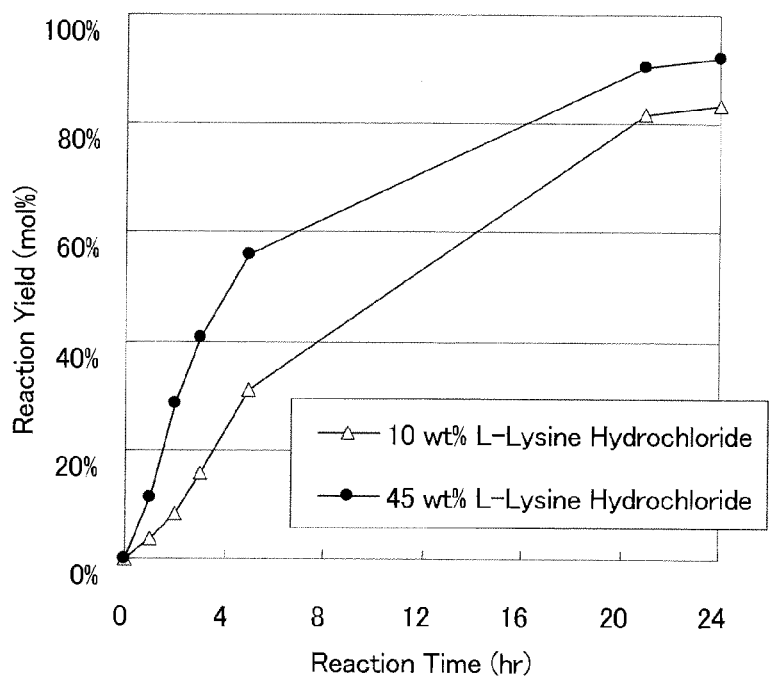
FIG. 2 is a diagram illustrating the relationships between time and yield in the reaction using 10 mass % and 45 mass % lysine hydrochlorides.

To a 300 mL flask, 120 g of a substrate solution was added: the substrate solution was prepared so that the final concentration of L-lysine monohydrochloride was 10 mass % or 45 mass %, and the final concentration of pyridoxal phosphate was 0.15 mM. Then, the collected bacterial cells of transformant W/pCADA obtained in Example 1 were added without treatment, allowing the reaction to start. By adding bacterial cells to the substrate solution, while the bacterial cells were treated with lysine hydrochloride, the reaction was allowed to start. The amounts of bacterial cells used were as follows: setting the ratio of the dry bacterial cell-based weight relative to the L-lysine monohydrochloride weight to 0.0012, 0.0144 g of bacterial cells (dry bacterial cell-based weight) was added to a substrate solution of 10 mass % L-lysine monohydrochloride, and 0.0648 g of bacterial cells (dry bacterial cell-based weight) was added to a substrate solution of 45 mass % L-lysine monohydrochloride. The reaction conditions were as follows: 37° C. and 200 rpm. The reaction results are shown in Table 6 and in FIG. 2.

TABLE 6

| | Reaction Yield(mol %) | |
|---|---|---|
| Reaction Time | 10 mass % L-lysine monohydrochloride | 45 mass % L-lysine monohydrochloride |
| 1 hour | 3.9 | 11.1 |
| 2 hours | 8.4 | 28.8 |
| 3 hours | 15.7 | 40.7 |
| 5 hours | 31.1 | 56.0 |
| 21 hours | 81.9 | 90.3 |
| 24 hours | 83.6 | 92.0 |

Untreated bacterial cells were added to the substrate solutions having respective concentrations of L-lysine hydrochloride, and the mixtures were allowed to react while giving the lysine hydrochloride treatment: while the 10 mass % L-lysine monohydrochloride resulted in the yield of 816 mol % with a reaction of 24 hours, the 45 mass % L-lysine monohydrochloride resulted in a yield of 92.0 mol % with a reaction of 24 hours, i.e., the reactivity improved.

Example 8

[Effects of Freeze-Thaw Treatment 1]

The collected bacterial cells of transformant W/pCADA obtained in Example 1 were suspended in water, thereby preparing a bacterial cell suspension having a respective dry bacterial cell-based concentrations shown in Table 7. The collected bacterial cells of Example 1 and prepared bacterial cell suspensions were frozen at temperatures shown in Table 7, and thereafter thawed at room temperature (about 25° C.). These bacterial cells were appropriately diluted with a diluent (10 mM of a sodium phosphate buffer solution (pH7.0) containing 0.15 mM pyridoxal phosphate and 5 g/L bovine albumin (manufactured by SIGMA)), and measurement of lysine decarboxylase activity was conducted using the obtained bacterial cell diluted solution. The results are shown in Table 7. In Comparative Example, results when using the untreated bacterial cells of Comparative Example 1 are shown.

TABLE 7

| Nos. of Comp. Ex. and Ex. | Freezing Temperature | Dry bacterial cell-based concentration | Bacterial Cell Activity | Relative Activity |
|---|---|---|---|---|
| Comp. Ex. 1 | (Without freeze-thaw treatment) | — | 1.44 | 1.00 |
| Ex. 8-1 | −10° C. | 3.0 mass % | 47.2 | 32.8 |
| | | 15 mass % | 47.0 | 32.6 |
| | | 25 mass % | 47.2 | 32.8 |

TABLE 7-continued

| Nos. of Comp. Ex. and Ex. | Freezing Temperature | Dry bacterial cell-based concentration | Bacterial Cell Activity | Relative Activity |
|---|---|---|---|---|
| Ex. 8-2 | −20° C. | 0.3 mass % | 48.5 | 33.7 |
| | | 1.2 mass % | 45.3 | 31.5 |
| | | 3.0 mass % | 48.1 | 33.4 |
| | | 15 mass % | 48.2 | 33.4 |
| | | 25 mass % | 49.6 | 34.5 |
| Ex. 8-3 | −30° C. | 0.3 mass % | 49.5 | 34.4 |
| | | 1.2 mass % | 45.7 | 31.8 |
| | | 3.0 mass % | 48.5 | 33.7 |
| | | 15 mass % | 48.1 | 33.4 |
| | | 25 mass % | 37.4 | 26.1 |
| Ex. 8-4 | −80° C. | 0.3 mass % | 55.6 | 38.6 |
| | | 1.2 mass % | 50.8 | 35.3 |
| | | 3.0 mass % | 49.8 | 34.6 |
| | | 15 mass % | 50.9 | 35.3 |
| | | 25 mass % | 19.4 | 13.5 |

The bacterial cell activity is indicated as the enzyme activity (U/mg dry cells) per 1 mg of dry bacterial cell-based weight. The relative activity is indicated setting the bacterial cell activity of Comparative Example 1 as 1.

By conducting freeze-thaw treatment, bacterial cell activity increased to 13.5 times or more.

Example 9

[Stability of Lysine Decarboxylase in Freeze-Thaw Treatment]

The bacterial cell diluted solution after freeze-thaw treatment obtained in Example 8 and the bacterial cell diluted solution obtained in Comparative Example 1 were disrupted with Bioruptor (manufactured by Olympus Corporation) in ice water for 5 minutes, and measurement of lysine decarboxylase activity was conducted using the obtained bacterial cell-disrupted solution. The results are shown in Table 8.

TABLE 8

| Nos. of Comp. Ex. and Ex. | Freezing Temperature | Dry bacterial cell-based concentration | Bacterial Cell Activity | Relative Activity |
|---|---|---|---|---|
| Comp. Ex. 2 | (Without freeze-thaw treatment) | — | 106.0 | 1.00 |
| Ex. 9-1 | −10° C. | 3.0 mass % | 98.8 | 0.93 |
| | | 15 mass % | 100.4 | 0.95 |
| | | 25 mass % | 96.9 | 0.91 |
| Ex. 9-2 | −20° C. | 0.3 mass % | 80.2 | 0.76 |
| | | 1.2 mass % | 88.3 | 0.83 |
| | | 3.0 mass % | 98.8 | 0.93 |
| | | 15 mass % | 100.4 | 0.95 |
| | | 25 mass % | 90.3 | 0.85 |
| Ex. 9-3 | −30° C. | 0.3 mass % | 84.6 | 0.80 |
| | | 1.2 mass % | 89.6 | 0.85 |
| | | 3.0 mass % | 101.0 | 0.95 |
| | | 15 mass % | 103.2 | 0.97 |
| | | 25 mass % | 107.1 | 1.01 |
| Ex. 9-4 | −80° C. | 0.3 mass % | 100.4 | 0.95 |
| | | 1.2 mass % | 103.8 | 0.98 |
| | | 3.0 mass % | 103.0 | 0.97 |
| | | 15 mass % | 106.0 | 1.00 |
| | | 25 mass % | 103.8 | 0.98 |

The bacterial cell activity is indicated as the enzyme activity (U/mg dry cells) per 1 mg of dry bacterial cell-based weight. The relative activity is indicated setting the bacterial cell activity of Comparative Example 2 as 1. The relative activity indicates lysine decarboxylase activity remaining rate after freeze-thaw treatment.

By setting the dry bacterial cell-based concentration at the time of freeze-thaw treatment to 3.0 mass %, activity remaining rate after the freeze-thaw treatment became 85% or more, and lysine decarboxylase showed high stability against freeze-thaw treatment.

Example 10

[Effects of Freeze-Thaw Treatment 2]

Figure 3:
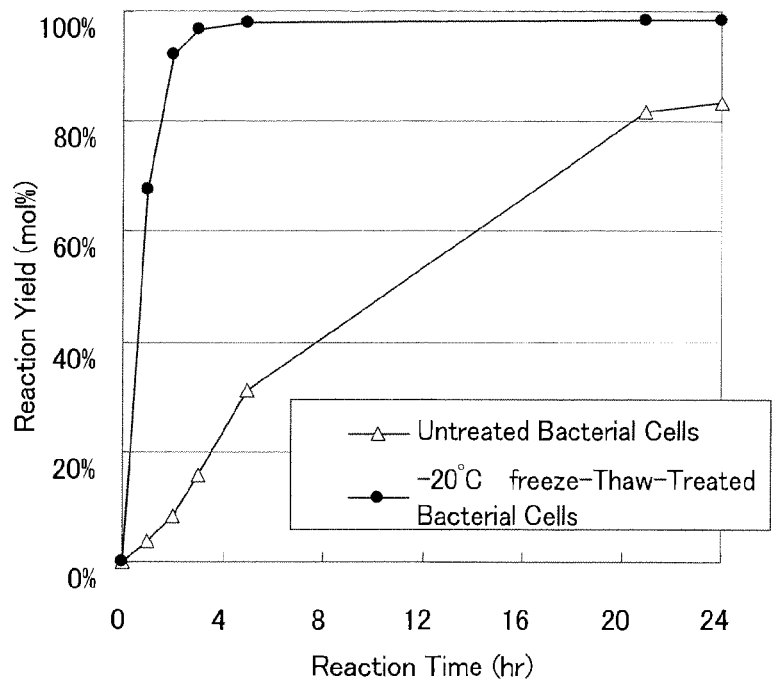
FIG. 3 is a diagram illustrating the relationships between time and yield in the reaction using untreated bacterial cells and −20° C. freeze-thaw-treated bacterial cells.

To a 300 mL flask, 120 g of a substrate solution was added: the substrate solution was prepared so that the final concentration of L-lysine monohydrochloride was 10 mass %, and the final concentration of pyridoxal phosphate was 0.15 mM. Then, the freeze-thaw-treated bacterial cells (dry bacterial cell-based weight 0.0144 g) prepared in Example 8 having a freezing temperature of −20° C. and a dry bacterial cell-based concentration of 25 mass % at the time of treatment or untreated bacterial cells (dry bacterial cell-based weight of 0.0144 g) of Comparative Example 1 were added, thereby allowing the reaction to start. The reaction conditions were as follows: 37° C. and 200 rpm. The reaction results are shown in Table 9 and in FIG. 3.

TABLE 9

| | Reaction Yield(mol %) | |
|---|---|---|
| Reaction Time | Untreated Bacterial Cells | −20° C. freeze-thaw-treated bacterial cells |
| 1 hour | 3.9 | 67.6 |
| 2 hours | 8.4 | 92.0 |
| 3 hours | 15.7 | 96.7 |
| 5 hours | 31.1 | 98.1 |
| 21 hours | 81.9 | 98.2 |
| 24 hours | 83.6 | 98.2 |

While the untreated bacterial cells resulted in a yield of 83.6 mol % with a reaction of 24 hours, the −20° C. freeze-thaw-treated bacterial cells resulted in a yield of 98.2 mol % with a reaction of 21 hour, i.e., reactivity improved.

Example 11

[Effects of Combination of Freeze-Thaw Treatment and Lysine Hydrochloride Treatment]

Figure 4:
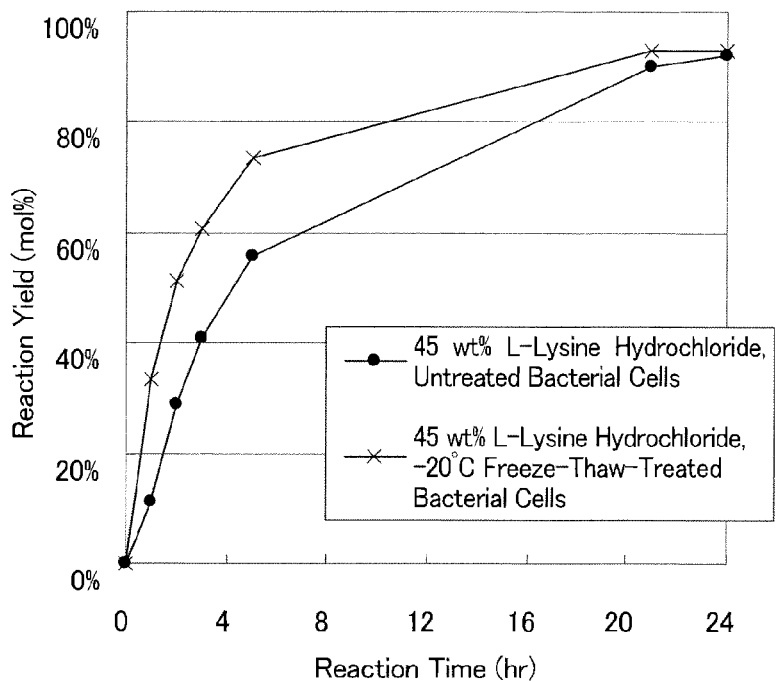
FIG. 4 is a diagram illustrating the relationships between time and yield in the reaction using 45 mass % of lysine hydrochloride, untreated bacterial cells and −20° C. freeze-thaw-treated bacterial cells.

To a 300 mL flask, 120 g of a substrate solution was added: the substrate solution was prepared so that the final concentration of L-lysine monohydrochloride was 45 mass % and the final concentration of pyridoxal phosphate was 0.15 mM. Then, the freeze-thaw-treated bacterial cells (dry bacterial cell-based weight 0.0648 g) prepared in Example 9 with a freezing temperature of −20° C. were added, thereby allowing the reaction to start. The reaction conditions were as follows: 37° C. and 200 rpm. The reaction results are shown in Table 10 and in FIG. 4. In comparison, the results when the untreated bacterial cell (dry bacterial cell-based weight 0.0648 g) of Comparative Example 1 were used are shown.

TABLE 10

| | Reaction Yield(mol %) | |
|---|---|---|
| Reaction Time | Untreated Bacterial Cells | −20° C. freeze-thaw-treated bacterial cells |
| 1 hour | 11.1 | 33.5 |
| 2 hours | 28.8 | 51.1 |
| 3 hours | 40.7 | 60.8 |
| 5 hours | 56.0 | 73.4 |

TABLE 10-continued

| | Reaction Yield(mol %) | |
|---|---|---|
| Reaction Time | Untreated Bacterial Cells | −20° C. freeze-thaw-treated bacterial cells |
| 21 hours | 90.3 | 93.0 |
| 24 hours | 92.0 | 93.1 |

While the untreated bacterial cells (effects of lysine hydrochloride treatment alone) gave a yield of 92.0 mol % with a reaction of 24 hours, the −20° C. freeze-thaw-treated bacterial cells (effects of combination of freeze-thaw treatment and lysine hydrochloride treatment) gave a yield of 93.1 mol % with a reaction of 24 hours, i.e., the reaction yield improved.

Furthermore, while the production rate at the initial phase of reaction of the untreated bacterial cell was a yield 11.1 mol % with a reaction of 1 hour, the production rate at the initial phase of reaction of the −20° C. freeze-thaw-treated bacterial cells (effects of combination of freeze-thaw treatment and lysine hydrochloride treatment) improved to about three times, i.e., a yield of 33.5 mol % with a reaction of 1 hour.

As the bacterial cells, the freeze-thaw-treated bacterial cells were used, and by allowing the reaction to progress while treating the freeze-thaw-treated bacterial cells with a high concentration (45 mass %) lysine monohydrochloride, the production rate and the reaction yield further improved.

Preparation Example 1

(1) Preparation of Bacterial Cell Diluted Solution

The collected bacterial cells of transformant W/pCADA s obtained in Example 1 were frozen at −20° C., and then thawed at room temperature (about 25° C.). The bacterial cells were appropriately diluted with water, thereby producing a bacterial cell diluted solution.

(2) Production of Aqueous Solution of Pentamethylenediamine

To a flask, 120 parts by mass of a substrate solution was added: the substrate solution was prepared so that the final concentration of L-lysine monohydrochloride (manufactured by Wako Pure Chemical Industries, Ltd.) was 45 mass %, and the final concentration of pyridoxal phosphate (manufactured by Wako Pure Chemical Industries, Ltd.) was 0.15 mmol/L. Then, the above-described W/pCADA bacterial cell-disrupted solution (charged dry bacterial cell-based weight 0.3 g) were added, thereby allowing the reaction to start. The reaction conditions were as follows: 37° C. and 200 rpm. The pH of the reaction liquid was adjusted to pH6 with a 6 mol/L hydrochloric acid. The reaction yield pentamethylenediamine after 24 hours reached 99%. The pH of the above-described reaction liquid after a reaction of 24 hours was adjusted to pH2 with a 6 mol/L hydrochloric acid, and 0.6 parts by mass of activated carbon (manufactured by Maura Kasei Kabushiki Kaisha powder activated carbon PM-SX) was added thereto. The mixture was stirred at 25° C. for 1 hour, and filtered through a filter paper (manufactured by ADVANTEC, 5C). Then, the filtrate was adjusted to pH12 with sodium hydroxide, thereby producing an aqueous solution of pentamethylenediamine (17.0 mass % aqueous solution).

[Extraction Rate with Presence/Absence of Heat Treatment]

Example 12

Preparation of Pentamethylenediamine (a)

To a separator funnel, 100 parts by mass of an aqueous solution of pentamethylenediamine and 100 parts by mass of n-butanol were charged, and the mixture was stirred for 10 minutes. Thereafter, the mixture was allowed to stand for 30 minutes. The lower layer, i.e., the aqueous layer, was discharged, and then the upper layer, i.e., the organic layer, was discharged. The extraction rate measured was 91.8%.

Then, a four-neck flask equipped with a thermometer, a distillation column, a condenser tube, and a nitrogen inlet tube was charged with 80 parts by mass of the extract of the organic layer, and with an oil bath temperature of 120° C. and under a reduced pressure of 10 kPa, n-butanol was distilled off, thereby obtaining pentamethylenediamine (a) having a purity of 99.9 mass %.

That is, pentamethylenediamine (a) was prepared without heat treating the aqueous solution of pentamethylenediamine, and by conducting solvent extraction with n-butanol, and further distilling off n-butanol.

Example 13

Preparation of Pentamethylenediamine (b)

A four-neck flask equipped with a stirrer, a thermometer, a reflux tube, and a nitrogen inlet tube was charged with 110 parts by mass of the aqueous solution of pentamethylenediamine obtained in Preparation Example 1, and water was distilled off under 38 kPa and at 80° C., thereby producing 19.6 mass % of an aqueous solution of pentamethylenediamine.

A separator funnel was charged with 100 parts by mass of the above-described aqueous solution of pentamethylenediamine and 100 parts by mass of n-butanol (extractant), and the mixture was stirred for 10 minutes. Thereafter, the mixture was allowed to stand for 30 minutes. Then, the organic layer (n-butanol including pentamethylenediamine) was discharged, and the extraction rate was measured. As a result, the extraction rate was 93.4%.

Then, n-butanol was distilled off under the same conditions and in the same manner as in Example 12, thereby producing pentamethylenediamine (b) having a purity of 99.6 mass %.

That is, pentamethylenediamine (b) was prepared by heat treating the aqueous solution of pentamethylenediamine at below 90° C., and also by conducting solvent extraction with n-butanol, and further by distilling off n-butanol.

Example 14

Preparation of Pentamethylenediamine (c)

A four-neck flask equipped with a stirrer, a thermometer, a reflux tube, and a nitrogen inlet tube was charged with 110 parts by mass of the aqueous solution of pentamethylenediamine obtained in Preparation Example 1, and water was distilled off under atmospheric pressure and at a reflux temperature (105° C.), thereby producing 19.4 mass % of an aqueous solution of pentamethylenediamine.

A separator funnel was charged with 100 parts by mass of the above-described aqueous solution of pentamethylenediamine and 100 parts by mass of n-butanol (extractant), and the mixture was stirred for 10 minutes. Thereafter, the mixture was allowed to stand for 30 minutes. Then, the organic layer (n-butanol including pentamethylenediamine) was discharged, and the extraction rate was measured. As a result, the extraction rate was 89.2%.

Then, n-butanol was distilled off under the same conditions and in the same manner as in Example 12, thereby producing pentamethylenediamine (c) having a purity of 99.2 mass %.

That is, pentamethylenediamine (c) was prepared by heat treating the aqueous solution of pentamethylenediamine at 90° C. or more, and also conducting solvent extraction with n-butanol, and further by distilling off n-butanol.

[Extraction Rate Depending on Different Extractant]

Example 15

Preparation of Pentamethylenediamine (d)

To a separator funnel, 100 parts by mass of an aqueous solution of pentamethylenediamine and 100 parts by mass of n-butanol were charged, and the mixture was stirred for 10 minutes. Thereafter, the mixture was allowed to stand for 30 minutes. The lower layer, i.e., the aqueous layer, was discharged, and then the upper layer, i.e., the organic layer, was discharged. The extraction rate measured was 91.7%.

Then, a four-neck flask equipped with a thermometer, a distillation column, a condenser tube, and a nitrogen inlet tube was charged with 80 parts by mass of the extract of the organic layer, and the extract was heated under normal pressure until the liquid temperature reached 139° C. to distill off water and n-butanol, thereby producing 17 parts by mass of a solution of 1,5-pentamethylenediamine in n-butanol. Then, a four-neck flask equipped with a thermometer, a distillation column, a condenser tube, and a nitrogen inlet tube was charged with 17 parts by mass of the n-butanol solution of 1,5-pentamethylenediamine, and the n-butanol solution of 1,5-pentamethylenediamine was heated under 1.7 kPa until the liquid temperature reached 65° C., thereby producing a distillate, i.e., pentamethylenediamine (d) (n-butanol solution of 1,5-pentamethylenediamine). The purity of pentamethylenediamine in pentamethylenediamine (d) was 33.5%.

Example 16

Preparation of Pentamethylenediamine (e)

To a separator funnel, 100 parts by mass of an aqueous solution of pentamethylenediamine and 100 parts by mass of isobutanol were charged, and the mixture was stirred for 10 minutes. Thereafter, the mixture was allowed to stand for 30 minutes. The lower layer, the aqueous layer was discharged, and then the upper layer, i.e., the organic layer was discharged. The extraction rate measured was 85.8%.

Then, a four-neck flask equipped with a thermometer, a distillation column, a condenser tube, and a nitrogen inlet tube was charged with 80 parts by mass of the extract of the organic layer, and the extract of the organic layer was heated under normal pressure until the liquid temperature reached 130° C. to distill off water and isobutanol, thereby producing 16 parts by mass of a solution of 1,5-pentamethylenediamine in isobutanol. Then, a four-neck flask equipped with a thermometer, a distillation column, a condenser tube, and a nitrogen inlet tube was charged with 16 parts by mass of the isobutanol solution of 1,5-pentamethylenediamine, and the isobutanol solution of 1,5-pentamethylenediamine was heated under 1.7 kPa until the liquid temperature reached 65° C., thereby producing a distillate, i.e., pentamethylenediamine (e) (isobutanol solution of 1,5-pentamethylenediamine). The purity of pentamethylenediamine in pentamethylenediamine (e) was 33.9%.

[Yield Depending on Different Extractants Thermal Decomposition Reaction]

Example 17

Production of Pentamethylene Diisocyanate (a)

An SUS-made autoclave equipped with a pressure control valve, a reflux condenser, a gas-liquid separator, and a stirrer was charged with a mixture of 152 parts by mass of pentamethylenediamine (d) (n-butanol solution of 1,5-pentamethylenediamine) obtained in Example 15, 72 parts by mass of urea, and 121 parts by mass of n-butanol, and the mixture was allowed to react for 3 hours with a nitrogen gas flow of 0.3 L per minute while stifling at 500 rpm and adjusting the internal pressure with a pressure control valve so as to keep the reaction temperature at 215° C. The obtained reaction liquid was subjected to reduced-pressure distillation under 0.5 KPa at 150° C. to cut the low-boiling-point components, thereby producing 150 parts by mass of bis(butoxycarbonylamino)pentane having a purity of 96.2 mass % with a yield of 95.6 mass %

Then, using a four-neck flask equipped with a rectifying column having a stirrer, a thermometer, and a condenser as a reactor, warm water of 80° C. was allowed to flow in the condenser, and a receiver was connected to a vacuum line with a cold trap cooling with cold acetone interposed therebetween. The flask was charged with 150 parts by mass of bis(butoxycarbonylamino)pentane, 150 parts by mass of Barrel process oil B-30 (manufactured by Matsumura Oil Co., Ltd.), and 0.3 parts by mass of dibutyltin dilaurate. After replacing the inside of the reaction system with nitrogen, the pressure was reduced to 3.0 kPa, and the temperature of the reaction liquid was increased to 250° C. to carry out thermal decomposition reaction for 2 hours, thereby producing 70 parts by mass of pentamethylene diisocyanate (a) having a purity of 99.9 mass %. The yield of the thermal decomposition reaction was 95.1 mass %, and the yield of pentamethylene diisocyanate (a) was 91.0 mass %.

Example 18

Production of Pentamethylene Diisocyanate (b)

An SUS-made autoclave equipped with a pressure control valve, a reflux condenser, a gas-liquid separator, and a stirrer was charged with a mixture of 150 parts by mass of pentamethylenediamine (e) (isobutanol solution of 1,5-pentamethylenediamine) obtained in Example 16, 72 parts by mass of urea, and 123 parts by mass of n-butanol, and the mixture was allowed to react for 3 hours with a nitrogen gas flow of 0.3 L per minute while stirring at 500 rpm and adjusting the internal pressure with a pressure control valve so as to keep the reaction temperature at 215° C. The obtained reaction liquid was subjected to reduced-pressure distillation under 0.5 KPa at 150° C. to cut the low-boiling point components, thereby producing 150 parts by mass of bis(butoxycarbonylamino)pentane having a purity of 89.8 mass % with a yield of 89.3 mass %.

Then, using a four-neck flask equipped with a rectifying column having a stirrer, a thermometer, and a condenser as a reactor, warm water of 80° C. was allowed to flow in the condenser, and a receiver was connected to a vacuum line with a cold trap cooling with cold acetone interposed therebetween. The flask was charged with 150 parts by mass of bis(butoxycarbonylamino)pentane, 150 parts by mass of Barrel process oil B-30 (manufactured by Matsumura Oil Co., Ltd.), and 0.3 parts by mass of dibutyltin dilaurate. After replacing the inside of the reaction system with nitrogen, the pressure was reduced to 3.0 kPa, and the temperature of the reaction liquid was increased to 250° C. to carry out thermal decomposition reaction for 2 hours, thereby producing 63 parts by mass of pentamethylene diisocyanate (b) having a purity of 99.9 mass %. The yield of the thermal decomposition reaction was 91.9 mass %, and the yield of pentamethylene diisocyanate (b) was 82.1 mass %.

Example 19

Production of Pentamethylene Diisocyanate (c)

An SUS-made autoclave equipped with a pressure control valve, a reflux condenser, a gas-liquid separator, and a stirrer was charged with a mixture of 51 parts by mass of pentamethylenediamine (a), 72 parts by mass of urea, and 222 parts by mass of n-butanol, and the mixture was allowed to react for 3 hours with a nitrogen gas flow of 0.3 L per minute while stirring at 500 rpm and adjusting the internal pressure with a pressure control valve so as to keep the reaction temperature at 215° C. The obtained reaction liquid was subjected to reduced-pressure distillation under 0.5 KPa at 150° C. to cut the low-boiling temperature components, thereby producing 150 parts by mass of bis(butoxycarbonylamino)pentane having a purity of 96.1%.

Then, using a four-neck flask equipped with a rectifying column having a stirrer, a thermometer, and a condenser as a reactor, warm water of 80° C. was allowed to flow in the condenser, and a receiver was connected to a vacuum line with a cold trap cooling with cold acetone interposed therebetween. The flask was charged with 70 parts by mass of bis(butoxycarbonylamino)pentane, 70 parts by mass of Barrel process oil B-30 (manufactured by Matsumura Oil Co., Ltd.), and 0.14 parts by mass of dibutyltin dilaurate. After replacing the inside of the reaction system with nitrogen, the pressure was reduced to 3.0 kPa, and the temperature of the reaction liquid was increased to 250° C. to carry out reaction for 2 hours. After the completion of reaction, the reaction liquid collected with the receiver was determined with gas chromatography. The result showed that pentamethylene diisocyanate (c) having a purity of 99.9 mass % was obtained.

Analysis conditions of gas chromatography are shown below.

Apparatus; GC-14B (manufactured by Shimadzu Corporation)
Column; UA-20EX-2.0F, 1.2 mmφ×20 m (manufactured by Frontier Laboratories Ltd.)
Oven temperature; held at 100° C. for 2 minutes, increased at 10° C./min from 100° C. to 240° C., held at 240° C. for 14 minutes
Inlet Temperature; 250° C.
Detector temperature; 250° C.
Carrier gas; Helium Example 20

Production of Pentamethylene Diisocyanate (d)

Relative to 100 parts by mass of the reaction liquid obtained in Example 19, 0.005 parts by mass of 2,6-di(tert-butyl)-4-methylphenol, 0.001 parts by mass of p-toluenesulfonamide, and 0.01 parts by mass of tris (tridecyl) phosphite were added, thereby producing pentamethylene diisocyanate (d) having a purity of 99.9 mass %.

Then, pentamethylene diisocyanate (d) was transferred to a sample bottle. After nitrogen purge, the pentamethylene diisocyanate (d) was allowed to stand in an oven of 50° C. for 14 days, thereby carrying out storage stability test. The purity of pentamethylene diisocyanate (d) after the test was 99.8 mass %.

Example 21

Production of Pentamethylene Diisocyanate (e)

Relative to 100 parts by mass of the reaction liquid obtained in Example 19, 0.005 parts by mass of 2,6-di(tert-butyl)-4-methylphenol was added, thereby producing pentamethylene diisocyanate (e) having a purity of 99.9 mass %.

Then, pentamethylene diisocyanate (e) was transferred to a sample bottle. After nitrogen purge, pentamethylene diisocyanate (e) was allowed to stand in an oven of 50° C. for 14 days, thereby carrying out storage stability test. The purity of pentamethylene diisocyanate (e) after the test was 99.4 mass %.

Example 22

Production of Pentamethylene Diisocyanate (f)

Pentamethylene diisocyanate (f) having a purity of 99.9 mass % was obtained in the same manner as in Example 19, except that instead of pentamethylenediamine (a), pentamethylenediamine (b) was used.

Example 23

Production of Pentamethylene Diisocyanate (g)

Pentamethylene diisocyanate (g) having a purity of 99.5 mass % was obtained in the same manner as in Example 19, except that instead of pentamethylenediamine (a), pentamethylenediamine (c) was used.

[Production of Polyisocyanate Composition]

Example 24

Production of Polyisocyanate Composition (A)

A four-neck flask equipped with a stirrer, a thermometer, a reflux tube, and a nitrogen inlet tube was charged with 500 parts by mass of pentamethylene diisocyanate (c) of Example 19, 0.25 parts by mass of 2,6-di(tert-butyl)-4-methylphenol, and 0.25 parts by mass of tris (tridecyl) phosphite, and the temperature was increased to 60° C. Then, 0.1 parts by mass of N-(2-hydroxypropyl)-N,N,N-trimethylammonium-2-ethylhexanoate was added thereto as a trimerization catalyst. After reaction for 1 hour, 0.12 parts by mass of o-toluenesulfonamide was added thereto (conversion rate of isocyanate group: 10 mass %). The obtained reaction liquid was passed through a thin film distillator (degree of vacuum 0.093 KPa, temperature 150° C.) to remove the unreacted pentamethylene diisocyanate, and relative to 100 parts by mass of the obtained composition, 0.02 parts by mass of o-toluenesulfonamide was added thereto, thereby producing polyisocyanate composition (A).

The polyisocyanate composition (A) had a pentamethylene diisocyanate concentration of 0.3 mass %, an isocyanate trimer concentration of 63 mass %, an isocyanate group concentration 1 of 25.9 mass %, a viscosity 1 at 25° C. of 1530 mPa·s, and a color 1 of APHA20. These values measured are shown in Table 11 as measured values before heat acceleration test.

Then, polyisocyanate composition (A) was transferred to a metal container. After nitrogen purge, polyisocyanate composition (A) was allowed to stand in an oven of 60° C. for 4 days, thereby carrying out heat acceleration test. The polyisocyanate composition after the test had an isocyanate group concentration 2 of 25.5 mass %, viscosity 2 at 25° C. of 1650 mPa·s, and a color 2 of APHA30. These measured values are shown in Table 11 as measured values after heat acceleration test.

Example 25

Production of Polyisocyanate Composition (B)

A four-neck flask equipped with a stirrer, a thermometer, a reflux tube, and a nitrogen inlet tube was charged with 500 parts by mass of pentamethylene diisocyanate (c) of Example 19, 24 parts by mass of isobutanol, 0.3 parts by mass of 2,6-di(t-butyl)-4-methylphenol, and 0.3 parts by mass of tris (tridecyl) phosphite, and the temperature was increased to 85° C., thereby carrying out urethane reaction for 3 hours. Then, 0.02 parts by mass of lead octylate as the allophanate-forming catalyst was added thereto, and the reaction was carried out until the isocyanate group concentration reached the calculated value. Thereafter, 0.02 parts by mass of o-toluenesulfonamide was added. The obtained reaction liquid was passed through a thin film distillator (degree of vacuum 0.093 KPa, temperature 150° C.) to remove the unreacted pentamethylene diisocyanate, and relative to 100 parts by mass of the obtained composition, 0.02 parts by mass of o-toluenesulfonamide was added thereto, thereby producing polyisocyanate composition (B).

The polyisocyanate composition (B) had a pentamethylene diisocyanate concentration of 0.2 mass %, an isocyanate group concentration 1 of 20.4 mass %, a viscosity 1 at 25° C. of 200 mPa·s, and a color 1 of APHA20. These values measured are shown in Table 11 as measured values before heat acceleration test.

Then, polyisocyanate composition (B) was transferred to a metal container. After nitrogen purge, polyisocyanate composition was allowed to stand in an oven of 60° C. for 4 days, thereby carrying out heat acceleration test. The polyisocyanate composition after the test had an isocyanate group concentration 2 of 19.9 mass %, a viscosity 2 at 25° C. of 220 mPa·s, and a color 2 of APHA30. These measured values are shown in Table 11 as measured values after heat acceleration test.

Example 26

Production of Polyisocyanate Composition (C)

A four-neck flask equipped with a stirrer, a thermometer, a reflux tube, and a nitrogen inlet tube was charged with 500 parts by mass of pentamethylene diisocyanate (c) of Example 19, 0.2 parts by mass of tris (tridecyl) phosphite, 8 parts by mass of trimethylphosphoric acid, and 5 parts by mass of water, and the temperature was increased to 130° C. The reaction was carried out until the isocyanate group concentration reached the calculated value. The obtained reaction liquid was passed through a thin film distillator (degree of vacuum 0.093 KPa, temperature 150° C.) to remove the unreacted pentamethylene diisocyanate, thereby producing polyisocyanate composition (C).

The polyisocyanate composition (C) had a pentamethylene diisocyanate concentration of 0.6 mass %, an isocyanate group concentration 1 of 24.8 mass %, a viscosity 1 at 25° C. of 2810 mPa·s, and a color 1 of APHA30. These values measured are shown in Table 11 as measured values before heat acceleration test.

Then, polyisocyanate composition (C) was transferred to a metal container. After nitrogen purge, polyisocyanate composition was allowed to stand in an oven of 60° C. for 4 days, thereby carrying out heat acceleration test. The polyisocyanate composition after the test had an isocyanate group concentration 2 of 24.0 mass %, a viscosity 2 at 25° C. of 3200 mPa·s, and a color 2 of APHA40. These measured values are shown in Table 11 as measured values after heat acceleration test.

Example 27

Production of Polyisocyanate Composition (D)

A four-neck flask equipped with a stirrer, a thermometer, a reflux tube, and a nitrogen inlet tube was charged with 500 parts by mass of pentamethylene diisocyanate (c) of Example 19, and as a low-molecular-weight polyol, 50 parts by mass of trimethylolpropane (abbreviation: TMP) (equivalent ratio (NCO/OH)=5.8). In a nitrogen atmosphere, the temperature was increased to 75° C., and it was confirmed that trimethylolpropane was dissolved. Thereafter, reaction was carried out at 83° C. until the isocyanate group concentration reached the calculated value.

Then, after the temperature of the reaction solution was decreased to 55° C., 350 parts by mass of a mixed extractant (n-hexane/ethyl acetate=90/10 (mass ratio)) was added thereto. The reaction solution was stirred for 10 min, and after the reaction solution was allowed to stand for 10 min, the extractant layer was removed. This extraction operation was repeated 4 times.

Thereafter, the extractant remained in the reaction liquid was removed from the obtained reaction liquid under reduced pressure, while heating to 80° C. Ethyl acetate was further added, and the polyisocyanate composition concentration was adjusted to 75 mass %, thereby producing polyisocyanate composition (D). The polyisocyanate composition (D) had a pentamethylene diisocyanate concentration of 0.3 mass %, an isocyanate group concentration 1 of 20.5 mass %, a viscosity 1 at 25° C. of 500 mPa·s, and a color 1 of APHA20. These values measured are shown in Table 11 as measured values before heat acceleration test.

Then, polyisocyanate composition (D) was transferred to a metal container. After nitrogen purge, the polyisocyanate composition was allowed to stand in an oven of 60° C. for 4 days, thereby carrying out heat acceleration test. The polyisocyanate composition after the test had an isocyanate group concentration 2 of 20.0 mass %, a viscosity 2 at 25° C. of 530 mPa·s, and a color 2 of APHA30. These measured values are shown in Table 11 as measured values after heat acceleration test.

Example 28

Production of Polyisocyanate Composition (E)

A four-neck flask equipped with a stirrer, a thermometer, a reflux tube, and a nitrogen inlet tube was charged with 500 parts by mass of pentamethylene diisocyanate (c) of Example 19, 0.3 parts by mass of 2,6-di(tert-butyl)-4-methylphenol, 0.3 parts by mass of tris (tridecyl) phosphite, and 130 parts by mass of methoxypolyethylene ether glycol having an average molecular weight of 400, and the mixture was allowed to react in a nitrogen atmosphere 85° C. for 3 hours. Then, 0.1 parts by mass of N-(2-hydroxypropyl)-N,N,N-trimethylammonium-2-ethylhexanoate was added thereto as a trimerization catalyst. After reaction for 1 hour, 0.12 parts by mass of o-toluenesulfonamide was added thereto (conversion rate of isocyanate group: 10 mass %). The obtained reaction liquid was passed through a thin film distillator (degree of vacuum 0.093 KPa, temperature 150° C.) to remove the unreacted pentamethylene diisocyanate, and relative to 100 parts by mass of the obtained composition, 0.02 parts by mass of o-toluenesulfonamide was added thereto, thereby producing polyisocyanate composition (E).

The polyisocyanate composition (E) had a pentamethylene diisocyanate concentration of 0.1 mass %, an isocyanate group concentration 1 of 13.2 mass %, a viscosity 1 at 25° C. of 280 mPa·s, and a color 1 of APHA20. These values measured are shown in Table 11 as measured values before heat acceleration test.

Then, polyisocyanate composition (E) was transferred to a metal container. After nitrogen purge, the polyisocyanate composition was allowed to stand in an oven of 60° C. for 4 days, thereby carrying out heat acceleration test. The polyisocyanate composition after the test had an isocyanate group concentration 2 of 12.8 mass %, a viscosity 2 at 25° C. of 310 mPa·s, and a color 2 of APHA30. These measured values are shown in Table 11 as measured values after heat acceleration test.

Example 29

Production of Polyisocyanate Composition (F)

A four-neck flask equipped with a stirrer, a thermometer, a reflux tube, and a nitrogen inlet tube was charged with 500 parts by mass of pentamethylene diisocyanate (d) of Example 20, 3.9 parts by mass of 1,3-butanediol (hereinafter may be referred to as 1,3-BG), 0.25 parts by mass of 2,6-di(tert-butyl)-4-methylphenol, and 0.25 parts by mass of tris (tridecyl) phosphite, and the mixture was allowed to react at 80° C. for 3 hours. After the temperature of this solution was increased to 60° C., as a trimerization catalyst, 0.1 parts by mass of N-(2-hydroxypropyl)-N,N,N-trimethylammonium-2-ethylhexanoate was added thereto. After reaction for 1 hour, 0.12 parts by mass of o-toluenesulfonamide was added thereto (conversion rate of isocyanate group: 10 mass %). The obtained reaction liquid was passed through a thin film distillator (degree of vacuum 0.093 KPa, temperature 150° C.) to remove the unreacted pentamethylene diisocyanate, and relative to 100 parts by mass of the obtained composition, 0.02 parts by mass of o-toluenesulfonamide was added thereto, thereby producing polyisocyanate composition (F).

The polyisocyanate composition (F) had a pentamethylene diisocyanate concentration of 0.3 mass %, an isocyanate trimer concentration of 45 mass %, an isocyanate group concentration 1 of 23.9 mass %, a viscosity 1 at 25° C. of 2000 mPa·s, and a color 1 of APHA20. These values measured are shown in Table 11 as measured values before heat acceleration test.

Then, polyisocyanate composition (F) was transferred to a metal container. After nitrogen purge, polyisocyanate composition was allowed to stand in an oven of 60° C. for 4 days, thereby carrying out heat acceleration test. The polyisocyanate composition after the test had an isocyanate group concentration 2 of 23.4 mass %, a viscosity 2 at 25° C. of 2200 mPa·s, and a color 2 of APHA30. These measured values are shown in Table 11 as measured values after heat acceleration test.

Example 30

Production of Polyisocyanate Composition (G)

Polyisocyanate composition (G) was obtained in the same manner as in Example 29, except that pentamethylene diisocyanate (e) of Example 21 was used instead of pentamethylene diisocyanate (d).

The polyisocyanate composition (G) had a pentamethylene diisocyanate concentration of 0.5 mass %, an isocyanate trimer concentration of 42 mass %, an isocyanate group concentration 1 of 22.3 mass %, a viscosity 1 at 25° C. of 2250 mPa·s, and a color 1 of APHA20. These values measured are shown in Table 11 as measured values before heat acceleration test.

Then, polyisocyanate composition (G) was transferred to a metal container. After nitrogen purge, the polyisocyanate composition was allowed to stand in an oven of 60° C. for 4 days, thereby carrying out heat acceleration test. The polyisocyanate composition after the test had an isocyanate group concentration 2 of 21.6 mass %, a viscosity 2 at 25° C. of 2670 mPa·s, and a color 2 of APHA30. These measured values are shown in Table 11 as measured values after heat acceleration test.

TABLE 11

| | | Ex. 24 | Ex. 25 | Ex. 26 | Ex. 27 | Ex. 28 |
|---|---|---|---|---|---|---|
| POLYISOCYANATE COMPOSITION | | A | B | C | D | E |
| Pentamethylene Diisocyanate | | c | c | c | c | c |
| Pentamethylene Diisocyanate Concentration (mass %) | | 0.3 | 0.2 | 0.6 | 0.3 | 0.1 |
| Before heat acceleration test | Isocyanate Group Concentration 1 (mass %) | 25.9 | 20.4 | 24.8 | 20.5 | 13.2 |
| | Viscosity 1 (mPa · s) | 1530 | 200 | 2810 | 500 | 280 |
| | Color 1 (—) | 20 | 20 | 30 | 20 | 20 |
| After heat acceleration test | Isocyanate Group Concentration 2 (mass %) | 25.5 | 19.9 | 24.0 | 20.0 | 12.8 |
| | Viscosity 2 (mPa · s) | 1650 | 220 | 3200 | 530 | 310 |
| | Color 2 (—) | 30 | 30 | 40 | 30 | 30 |
| Reduction Rate (%) of Isocyanate Group Concentration After heat acceleration test | | 2 | 2 | 3 | 2 | 3 |
| Increase Rate (%) of Viscosity After heat acceleration test | | 8 | 10 | 14 | 6 | 11 |
| Changes in color After heat acceleration test (color 2 − color 1) | | 10 | 10 | 10 | 10 | 10 |

| | | Ex. 29 | Ex. 30 | Ex. 31 | Ex. 32 |
|---|---|---|---|---|---|
| POLYISOCYANATE COMPOSITION | | F | G | H | I |
| Pentamethylene Diisocyanate | | d | e | f | g |
| Pentamethylene Diisocyanate Concentration (mass %) | | 0.3 | 0.5 | 0.3 | 0.5 |

TABLE 11-continued

|  |  |  |  |  |  |
|---|---|---|---|---|---|
| Before heat acceleration test | Isocyanate Group Concentration 1 (mass %) | 23.9 | 22.3 | 25.7 | 23.6 |
|  | Viscosity1 (mPa · s) | 2000 | 2250 | 1620 | 2050 |
|  | Color 1 (—) | 20 | 20 | 20 | 40 |
| After heat acceleration test | Isocyanate Group Concentration 2 (mass %) | 23.4 | 21.6 | 25.2 | 22.4 |
|  | Viscosity2 (mPa · s) | 2200 | 2670 | 1780 | 2500 |
|  | Color 2 (—) | 30 | 30 | 30 | 60 |
| Reduction Rate (%) of Isocyanate Group Concentration After heat acceleration test |  | 2 | 3 | 2 | 5 |
| Increase Rate (%) of Viscosity After heat acceleration test |  | 10 | 19 | 10 | 22 |
| Changes in color After heat acceleration test (color 2 − color 1) |  | 10 | 10 | 10 | 20 |

(Consideration)

In the pentamethylene diisocyanate (d) used in Example 29, an antioxidant, an acid compound, and a compound having a sulfonamide group were blended, and therefore even if the pentamethylene diisocyanate (d) was stored under high temperature in advance (50° C., for 14 days), a polyisocyanate composition obtained by using the pentamethylene diisocyanate achieved the same degree of storage stability as that of those other polyisocyanate compositions obtained by using unstored pentamethylene diisocyanate.

Example 31

Production of Polyisocyanate Composition (H)

Polyisocyanate composition (H) was obtained in the same manner as in Example 24, except that pentamethylene diisocyanate (f) of Example 22 was used instead of pentamethylene diisocyanate (c).

The polyisocyanate composition (H) had a pentamethylene diisocyanate concentration of 0.3 mass %, an isocyanate trimer concentration of 62 mass %, an isocyanate group concentration 1 of 25.7 mass %, a viscosity 1 at 25° C. of 1620 mPa·s, and a color 1 of APHA20. These values measured are shown in Table 11 as measured values before heat acceleration test.

Then, polyisocyanate composition (H) was transferred to a metal container. After nitrogen purge, the polyisocyanate composition was allowed to stand in an oven of 60° C. for 4 days, thereby carrying out heat acceleration test. The polyisocyanate composition after the test had an isocyanate group concentration 2 of 25.2 mass %, a viscosity 2 at 25° C. of 1780 mPa·s, and a color 2 of APHA30. These measured values are shown in Table 11 as measured values after heat acceleration test.

Example 32

Production of Polyisocyanate Composition (I)

The trimerization reaction was carried out in the same manner as in Example 24 using pentamethylene diisocyanate (g) of Example 23 instead of pentamethylene diisocyanate (c). However, because it was confirmed that the reaction rate was low from the measurement of the isocyanate group concentration, 0.1 parts by mass of N-(2-hydroxypropyl)-N,N,N-trimethylammonium-2-ethylhexanoate was added, thereby producing polyisocyanate composition (I).

The polyisocyanate composition (I) had a pentamethylene diisocyanate concentration of 0.5 mass %, an isocyanate trimer concentration of 55 mass %, an isocyanate group concentration 1 of 23.6 mass %, a viscosity 1 at 25° C. of 2050 mPa·s, and a color 1 of APHA40. These values measured are shown in Table 11 as measured values before heat acceleration test.

Then, polyisocyanate composition (I) was transferred to a metal container. After nitrogen purge, the polyisocyanate composition was allowed to stand in an oven of 60° C. for 4 days, thereby carrying out heat acceleration test. The polyisocyanate composition after the test had an isocyanate group concentration 2 of 22.4 mass %, a viscosity 2 at 25° C. of 2500 mPa·s, and a color 2 of APHA60. These measured values are shown in Table 11 as measured values after heat acceleration test.

Example 33

Production of Polyurethane Resin (A)

The polyisocyanate composition (A) obtained in Example 24, and acrylic polyol (manufactured by Mitsui Chemicals, trade name: TAKELAC to UA-702, in the following, abbreviated as UA-702) were blended so that the equivalent ratio (NCO/OH) of the isocyanate group in the polyisocyanate composition relative to the hydroxyl group in the acrylic polyol was 1.0. The mixture was stirred at 23° C. for 90 seconds, thereby producing a reaction mixture. Then, the reaction mixture was applied to a standard test plate (type: electrolytic tinplate, in the following, abbreviated as test plate) in conformity with JIS G 3303, and thereafter, cured at 80° C. for 30 min, and further at 110° C. for 1 hour, thereby producing a polyurethane resin (A) having a thickness of about 45 μm.

The obtained polyurethane resin (A) was allowed to stand at 23° C. in a room having a relative humidity of 55% for 7 days.

Physical Property Evaluation

The Martens hardness, tensile strength, solvent resistance, and scratch hardness of the polyurethane resin (hereinafter abbreviated as coating) obtained in Example 33 were measured in the following method.

<Martens Hardness (Unit: $N/mm^2$)>

The Martens hardness (HMT115) of the coating that was in close contact with the test plate was measured under the following conditions using a Dynamic Ultra Micro Hardness Tester (manufactured by Shimadzu Corporation, DUH-211). Type of indenter: Triangular 115, est mode: Load-unload test, Test Force: 10.00 mN, Loading Rate: 3.0 mN/sec, Holding Time: 10 sec.

The test result showed a Martens hardness of $128 N/mm^2$.

<Tensile Strength (TS) (Unit: MPa)>

The coating was punched out into a size of a width of 1 cm, and a length of 10 cm with a dumbbell. Then, this test sample was subjected to tensile test using tensile compression tester (manufactured by INTESCO co., Ltd., Model205N) with the following conditions: 23° C., tensile speed 10 mm/min, distance between chucks 50 mm. The tensile strength (TS) was measured in this manner.

The test result showed that the tensile strength (TS) was 54 MPa.

<Solvent Resistance (Unit: Times)>

A cotton swab sufficiently impregnated with a test solution was placed on the coating that is in close contact with the test plate, and allowed to go back and forth in a distance of about 1 cm while a constant load is applied. The above operation was repeated several times, and the test was terminated at the point when a damage was found on the coating. The outbound was counted once, and the inbound was counted as once (back and forth), and the number until a damage is found on the coating is regarded as SOLVENT RESISTANCE. The test solutions used were ethyl acetate, toluene, and methyl ethyl ketone.

The result showed that the number of times until a damage is found is, with ethyl acetate, 160 times; with toluene, 290 times; and with methyl ethyl ketone, 120 times.

INDUSTRIAL APPLICABILITY

A method for producing 1,5-pentamethylenediamine, and a method for producing 1,5-pentamethylene diisocyanate are suitably used in various industrial fields, and 1,5-pentamethylenediamine, 1,5-pentamethylene diisocyanate, polyisocyanate composition, and a polyurethane resin obtained by these methods are suitably used as an industrial material in various industries.

The invention claimed is:

1. A method for producing 1,5-pentamethylene diisocyanate, comprising:
   obtaining an aqueous solution containing 1,5-pentamethylenediamine by lysine decarboxylation reaction;
   mixing, without heating the aqueous solution, the obtained aqueous solution containing 1,5-pentamethylenediamine as it is with a monohydric alcohol having 4 to 7 carbon atoms as an extractant at a mixing ratio of the extractant of 50 to 200 parts by mass relative to 100 parts by mass of the aqueous solution containing 1,5-pentamethylenediamine per extraction;
   carrying out liquid-liquid extraction at 15 to 50 °C. to obtain 1,5-pentamethylenediamine; and
   phosgenating the obtained 1,5-pentamethylenediamine.

* * * * *

SEQUENCE LISTING

```
<160> NUMBER OF SEQ ID NOS: 4

<210> SEQ ID NO 1
<211> LENGTH: 47
<212> TYPE: DNA
<213> ORGANISM: Artificial
<220> FEATURE:
<223> OTHER INFORMATION: Primer

<400> SEQUENCE: 1
aaggtaccac aaaaaggata aaacaatgaa cgttattgca atattga            47

<210> SEQ ID NO 2
<211> LENGTH: 30
<212> TYPE: DNA
<213> ORGANISM: Artificial
<220> FEATURE:
<223> OTHER INFORMATION: Primer

<400> SEQUENCE: 2
agtctagatt atttttgct ttcttctttc                                30

<210> SEQ ID NO 3
<211> LENGTH: 2177
<212> TYPE: DNA
<213> ORGANISM: Escherichia coli
<220> FEATURE:
<221> NAME/KEY: CDS
<222> LOCATION: (24)..(2171)

<400> SEQUENCE: 3
ggtaccacaa aaaggataaa aca atg aac gtt att gca ata ttg aat cac atg     53
                       Met Asn Val Ile Ala Ile Leu Asn His Met
                         1               5                  10 ggg gtt tat ttt aaa gaa gaa ccc atc cgt gaa ctt cat cgc gcg ctt      101
Gly Val Tyr Phe Lys Glu Glu Pro Ile Arg Glu Leu His Arg Ala Leu
             15                  20                  25 gaa cgt ctg aac ttc cag att gtt tac ccg aac gac cgt gac gac tta      149
Glu Arg Leu Asn Phe Gln Ile Val Tyr Pro Asn Asp Arg Asp Asp Leu
         30                  35                  40 tta aaa ctg atc gaa aac aat gcg cgt ctg tgc ggc gtt att ttt gac      197
Leu Lys Leu Ile Glu Asn Asn Ala Arg Leu Cys Gly Val Ile Phe Asp
     45                  50                  55 tgg gat aaa tat aat ctc gag ctg tgc gaa gaa att agc aaa atg aac      245
Trp Asp Lys Tyr Asn Leu Glu Leu Cys Glu Glu Ile Ser Lys Met Asn
 60                  65                  70 gag aac ctg ccg ttg tac gcg ttc gct aat acg tat tcc act ctc gat      293
Glu Asn Leu Pro Leu Tyr Ala Phe Ala Asn Thr Tyr Ser Thr Leu Asp
 75                  80                  85                  90
```

```
gta agc ctg aat gac ctg cgt tta cag att agc ttc ttt gaa tat gcg      341
Val Ser Leu Asn Asp Leu Arg Leu Gln Ile Ser Phe Phe Glu Tyr Ala
             95                 100                 105 ctg ggt gct gct gaa gat att gct aat aag atc aag cag acc act gac      389
Leu Gly Ala Ala Glu Asp Ile Ala Asn Lys Ile Lys Gln Thr Thr Asp
        110                 115                 120 gaa tat atc aac act att ctg cct ccg ctg act aaa gca ctg ttt aaa      437
Glu Tyr Ile Asn Thr Ile Leu Pro Pro Leu Thr Lys Ala Leu Phe Lys
            125                 130                 135 tat gtt cgt gaa ggt aaa tat act ttc tgt act cct ggt cac atg ggc      485
Tyr Val Arg Glu Gly Lys Tyr Thr Phe Cys Thr Pro Gly His Met Gly
        140                 145                 150 ggt act gca ttc cag aaa agc ccg gta ggt agc ctg ttc tat gat ttc      533
Gly Thr Ala Phe Gln Lys Ser Pro Val Gly Ser Leu Phe Tyr Asp Phe
155                 160                 165                 170 ttt ggt ccg aat acc atg aaa tct gat att tcc att tca gta tct gaa      581
Phe Gly Pro Asn Thr Met Lys Ser Asp Ile Ser Ile Ser Val Ser Glu
                175                 180                 185 ctg ggt tct ctg ctg gat cac agt ggt cca cac aaa gaa gca gaa cag      629
Leu Gly Ser Leu Leu Asp His Ser Gly Pro His Lys Glu Ala Glu Gln
            190                 195                 200 tat atc gct cgc gtc ttt aac gca gac cgc agc tac atg gtg acc aac      677
Tyr Ile Ala Arg Val Phe Asn Ala Asp Arg Ser Tyr Met Val Thr Asn
        205                 210                 215 ggt act tcc act gcg aac aaa att gtt ggt atg tac tct gct cca gca      725
Gly Thr Ser Thr Ala Asn Lys Ile Val Gly Met Tyr Ser Ala Pro Ala
    220                 225                 230 ggc agc acc att ctg att gac cgt aac tgc cac aaa tcg ctg acc cac      773
Gly Ser Thr Ile Leu Ile Asp Arg Asn Cys His Lys Ser Leu Thr His
235                 240                 245                 250 ctg atg atg atg agc gat gtt acg cca atc tat ttc cgc ccg acc cgt      821
Leu Met Met Met Ser Asp Val Thr Pro Ile Tyr Phe Arg Pro Thr Arg
                255                 260                 265 aac gct tac ggt att ctt ggt ggt atc cca cag agt gaa ttc cag cac      869
Asn Ala Tyr Gly Ile Leu Gly Gly Ile Pro Gln Ser Glu Phe Gln His
            270                 275                 280 gct acc att gct aag cgc gtg aaa gaa aca cca aac gca acc tgg ccg      917
Ala Thr Ile Ala Lys Arg Val Lys Glu Thr Pro Asn Ala Thr Trp Pro
        285                 290                 295 gta cat gct gta att acc aac tct acc tat gat ggt ctg ctg tac aac      965
Val His Ala Val Ile Thr Asn Ser Thr Tyr Asp Gly Leu Leu Tyr Asn
    300                 305                 310 acc gac ttc atc aag aaa aca ctg gat gtg aaa tcc atc cac ttt gac     1013
Thr Asp Phe Ile Lys Lys Thr Leu Asp Val Lys Ser Ile His Phe Asp
315                 320                 325                 330 tcc gcg tgg gtg cct tac acc aac ttc tca ccg att tac gaa ggt aaa     1061
Ser Ala Trp Val Pro Tyr Thr Asn Phe Ser Pro Ile Tyr Glu Gly Lys
                335                 340                 345 tgc ggt atg agc ggt ggc cgt gta gaa ggg aaa gtg att tac gaa acc     1109
Cys Gly Met Ser Gly Gly Arg Val Glu Gly Lys Val Ile Tyr Glu Thr
            350                 355                 360 cag tcc act cac aaa ctg ctg gcg gcg ttc tct cag gct tcc atg atc     1157
Gln Ser Thr His Lys Leu Leu Ala Ala Phe Ser Gln Ala Ser Met Ile
        365                 370                 375 cac gtt aaa ggt gac gta aac gaa gaa acc ttt aac gaa gcc tac atg     1205
His Val Lys Gly Asp Val Asn Glu Glu Thr Phe Asn Glu Ala Tyr Met
    380                 385                 390 atg cac acc acc act tct ccg cac tac ggt atc gtg gcg tcc act gaa     1253
Met His Thr Thr Thr Ser Pro His Tyr Gly Ile Val Ala Ser Thr Glu
395                 400                 405                 410
```

```
acc gct gcg gcg atg atg aaa ggc aat gca ggt aag cgt ctg atc aac    1301
Thr Ala Ala Ala Met Met Lys Gly Asn Ala Gly Lys Arg Leu Ile Asn
            415                 420                 425 ggt tct att gaa cgt gcg atc aaa ttc cgt aaa gag atc aaa cgt ctg    1349
Gly Ser Ile Glu Arg Ala Ile Lys Phe Arg Lys Glu Ile Lys Arg Leu
        430                 435                 440 aga acg gaa tct gat ggc tgg ttc ttt gat gta tgg cag ccg gat cat    1397
Arg Thr Glu Ser Asp Gly Trp Phe Phe Asp Val Trp Gln Pro Asp His
    445                 450                 455 atc gat acg act gaa tgc tgg ccg ctg cgt tct gac agc acc tgg cac    1445
Ile Asp Thr Thr Glu Cys Trp Pro Leu Arg Ser Asp Ser Thr Trp His
460                 465                 470 ggc ttc aaa aac atc gat aac gag cac atg tat ctt gac ccg atc aaa    1493
Gly Phe Lys Asn Ile Asp Asn Glu His Met Tyr Leu Asp Pro Ile Lys
475                 480                 485                 490 gtc acc ctg ctg act ccg ggg atg gaa aaa gac ggc acc atg agc gac    1541
Val Thr Leu Leu Thr Pro Gly Met Glu Lys Asp Gly Thr Met Ser Asp
            495                 500                 505 ttt ggt att ccg gcc agc atc gtg gcg aaa tac ctc gac gaa cat ggc    1589
Phe Gly Ile Pro Ala Ser Ile Val Ala Lys Tyr Leu Asp Glu His Gly
        510                 515                 520 atc gtt gtt gag aaa acc ggt ccg tat aac ctg ctg ttc ctg ttc agc    1637
Ile Val Val Glu Lys Thr Gly Pro Tyr Asn Leu Leu Phe Leu Phe Ser
    525                 530                 535 atc ggt atc gat aag acc aaa gca ctg agc ctg ctg cgt gct ctg act    1685
Ile Gly Ile Asp Lys Thr Lys Ala Leu Ser Leu Leu Arg Ala Leu Thr
540                 545                 550 gac ttt aaa cgt gcg ttc gac ctg aac ctg cgt gtg aaa aac atg ctg    1733
Asp Phe Lys Arg Ala Phe Asp Leu Asn Leu Arg Val Lys Asn Met Leu
555                 560                 565                 570 ccg tct ctg tat cgt gaa gat cct gaa ttc tat gaa aac atg cgt att    1781
Pro Ser Leu Tyr Arg Glu Asp Pro Glu Phe Tyr Glu Asn Met Arg Ile
            575                 580                 585 cag gaa ctg gct cag aat atc cac aaa ctg att gtt cac cac aat ctg    1829
Gln Glu Leu Ala Gln Asn Ile His Lys Leu Ile Val His His Asn Leu
        590                 595                 600 ccg gat ctg atg tat cgc gca ttt gaa gtg ctg ccg acg atg gta atg    1877
Pro Asp Leu Met Tyr Arg Ala Phe Glu Val Leu Pro Thr Met Val Met
    605                 610                 615 act ccg tat gct gca ttc cag aaa gag ctg cac ggt atg acc gaa gaa    1925
Thr Pro Tyr Ala Ala Phe Gln Lys Glu Leu His Gly Met Thr Glu Glu
620                 625                 630 gtt tac ctc gac gaa atg gta ggt cgt att aac gcc aat atg atc ctt    1973
Val Tyr Leu Asp Glu Met Val Gly Arg Ile Asn Ala Asn Met Ile Leu
635                 640                 645                 650 ccg tac ccg ccg gga gtt cct ctg gta atg ccg ggt gaa atg atc acc    2021
Pro Tyr Pro Pro Gly Val Pro Leu Val Met Pro Gly Glu Met Ile Thr
            655                 660                 665 gaa gaa agc cgt ccg gtt ctg gag ttc ctg cag atg ctg tgt gaa atc    2069
Glu Glu Ser Arg Pro Val Leu Glu Phe Leu Gln Met Leu Cys Glu Ile
        670                 675                 680 ggc gct cac tat ccg ggc ttt gaa acc gat att cac ggt gca tac cgt    2117
Gly Ala His Tyr Pro Gly Phe Glu Thr Asp Ile His Gly Ala Tyr Arg
    685                 690                 695 cag gct gat ggc cgc tat acc gtt aag gta ttg aaa gaa gaa agc aaa    2165
Gln Ala Asp Gly Arg Tyr Thr Val Lys Val Leu Lys Glu Glu Ser Lys
700                 705                 710 aaa taa tctaga                                                      2177
Lys
```

715

<210> SEQ ID NO 4
<211> LENGTH: 715
<212> TYPE: PRT
<213> ORGANISM: Escherichia coli

<400> SEQUENCE: 4

```
Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
            20                  25                  30

Ile Val Tyr Pro Asn Asp Arg Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95

Arg Leu Gln Ile Ser Phe Phe Glu Tyr Ala Leu Gly Ala Ala Glu Asp
            100                 105                 110

Ile Ala Asn Lys Ile Lys Gln Thr Thr Asp Glu Tyr Ile Asn Thr Ile
        115                 120                 125

Leu Pro Pro Leu Thr Lys Ala Leu Phe Lys Tyr Val Arg Glu Gly Lys
    130                 135                 140

Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Gln Tyr Ile Ala Arg Val Phe
        195                 200                 205

Asn Ala Asp Arg Ser Tyr Met Val Thr Asn Gly Thr Ser Thr Ala Asn
    210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

Val Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
        275                 280                 285

Val Lys Glu Thr Pro Asn Ala Thr Trp Pro Val His Ala Val Ile Thr
    290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
            340                 345                 350

Arg Val Glu Gly Lys Val Ile Tyr Glu Thr Gln Ser Thr His Lys Leu
        355                 360                 365
```

-continued

```
Leu Ala Ala Phe Ser Gln Ala Ser Met Ile His Val Lys Gly Asp Val
    370                 375                 380
Asn Glu Glu Thr Phe Asn Glu Ala Tyr Met Met His Thr Thr Thr Ser
385                 390                 395                 400
Pro His Tyr Gly Ile Val Ala Ser Thr Glu Thr Ala Ala Ala Met Met
            405                 410                 415
Lys Gly Asn Ala Gly Lys Arg Leu Ile Asn Gly Ser Ile Glu Arg Ala
                420                 425                 430
Ile Lys Phe Arg Lys Glu Ile Lys Arg Leu Arg Thr Glu Ser Asp Gly
        435                 440                 445
Trp Phe Phe Asp Val Trp Gln Pro Asp His Ile Asp Thr Thr Glu Cys
    450                 455                 460
Trp Pro Leu Arg Ser Asp Ser Thr Trp His Gly Phe Lys Asn Ile Asp
465                 470                 475                 480
Asn Glu His Met Tyr Leu Asp Pro Ile Lys Val Thr Leu Leu Thr Pro
            485                 490                 495
Gly Met Glu Lys Asp Gly Thr Met Ser Asp Phe Gly Ile Pro Ala Ser
            500                 505                 510
Ile Val Ala Lys Tyr Leu Asp Glu His Gly Ile Val Val Glu Lys Thr
        515                 520                 525
Gly Pro Tyr Asn Leu Leu Phe Leu Phe Ser Ile Gly Ile Asp Lys Thr
    530                 535                 540
Lys Ala Leu Ser Leu Leu Arg Ala Leu Thr Asp Phe Lys Arg Ala Phe
545                 550                 555                 560
Asp Leu Asn Leu Arg Val Lys Asn Met Leu Pro Ser Leu Tyr Arg Glu
                565                 570                 575
Asp Pro Glu Phe Tyr Glu Asn Met Arg Ile Gln Glu Leu Ala Gln Asn
            580                 585                 590
Ile His Lys Leu Ile Val His His Asn Leu Pro Asp Leu Met Tyr Arg
        595                 600                 605
Ala Phe Glu Val Leu Pro Thr Met Val Met Thr Pro Tyr Ala Ala Phe
    610                 615                 620
Gln Lys Glu Leu His Gly Met Thr Glu Glu Val Tyr Leu Asp Glu Met
625                 630                 635                 640
Val Gly Arg Ile Asn Ala Asn Met Ile Leu Pro Tyr Pro Pro Gly Val
                645                 650                 655
Pro Leu Val Met Pro Gly Glu Met Ile Thr Glu Glu Ser Arg Pro Val
            660                 665                 670
Leu Glu Phe Leu Gln Met Leu Cys Glu Ile Gly Ala His Tyr Pro Gly
        675                 680                 685
Phe Glu Thr Asp Ile His Gly Ala Tyr Arg Gln Ala Asp Gly Arg Tyr
    690                 695                 700
Thr Val Lys Val Leu Lys Glu Glu Ser Lys Lys
705                 710                 715
```